(12) United States Patent
Menchaca et al.

(10) Patent No.: US 9,072,501 B2
(45) Date of Patent: Jul. 7, 2015

(54) MICRO-ORIFICE SURGICAL ACCESS SYSTEM

(71) Applicant: Regents of University of Minnesota, Saint Paul, MN (US)

(72) Inventors: Hector J. Menchaca, Apple Valley, MN (US); Van N. Michalek, Arden Hills, MN (US); Nestor B. Suguitani, Sao Paulo (BR); Henry Buchwald, Edina, MN (US); Mitsuhiro Oura, Minneapolis, MN (US); Arthur G. Erdman, New Brighton, MN (US)

(73) Assignee: Regents of the University of Minnesota, Saint Paul, MN (US)

(*) Notice: Subject to any disclaimer, the term of this patent is extended or adjusted under 35 U.S.C. 154(b) by 88 days.

(21) Appl. No.: 13/833,156

(22) Filed: Mar. 15, 2013

(65) Prior Publication Data

US 2014/0275801 A1    Sep. 18, 2014

(51) Int. Cl.
*A61B 1/32* (2006.01)
*A61B 17/02* (2006.01)
*A61B 17/34* (2006.01)
*A61B 19/00* (2006.01)

(52) U.S. Cl.
CPC ............ *A61B 17/02* (2013.01); *A61B 17/3423* (2013.01); *A61B 17/0218* (2013.01); *A61B 17/0293* (2013.01); *A61B 17/3431* (2013.01); *A61B 2017/3427* (2013.01); *A61B 2017/345* (2013.01); *A61B 2019/521* (2013.01)

(58) Field of Classification Search
CPC ........ A61B 17/02–17/0293; A61B 2017/0218; A61B 2017/0237; A61B 2017/0256–2017/0275
USPC .................................................. 600/201–249
See application file for complete search history.

(56) References Cited

U.S. PATENT DOCUMENTS

| | | | |
|---|---|---|---|
| 4,130,113 A | * | 12/1978 | Graham ........................ 600/224 |
| 5,279,575 A | | 1/1994 | Sugarbaker |
| 5,505,690 A | | 4/1996 | Patton et al. |

(Continued)

FOREIGN PATENT DOCUMENTS

| | | |
|---|---|---|
| DE | 19828099 | 12/1999 |
| GB | 391204 | 4/1933 |
| WO | 2010019597 | 2/2010 |

OTHER PUBLICATIONS

The International Search Report and Written Opinion of the IA for PCT/US2014/028574 mailed May 22, 2014.

*Primary Examiner* — Matthew Lawson
(74) *Attorney, Agent, or Firm* — Dicke, Billig & Czaja, PLLC

(57) ABSTRACT

A surgical access system including an access port device. The port device has a port member, a plurality of blades, and an articulation mechanism. The blades are circumferentially arranged about a longitudinal axis of the port member to collectively define an access region. The articulation mechanism defines a pivot point along a length of each blade, and is operable to articulate the blades between collapsed and expanded states. The blade tips collectively define a diameter in the collapsed state that is less than that in the expanded state. The blades rotate about the corresponding pivot point, and the pivot points move longitudinally relative to the port member, in transitioning between the contracted and expanded states. Light source(s) can be integrated with the blades or separately provided to enhance surgical field visibility.

22 Claims, 27 Drawing Sheets

(56) References Cited

U.S. PATENT DOCUMENTS

| | | |
|---|---|---|
| 5,928,139 A | 7/1999 | Koros et al. |
| 6,354,995 B1 | 3/2002 | Hoftman et al. |
| 6,450,952 B1 | 9/2002 | Rioux et al. |
| 6,504,985 B2 | 1/2003 | Parker et al. |
| 7,261,688 B2 | 8/2007 | Smith et al. |
| 7,344,495 B2 | 3/2008 | Ravikumar et al. |
| 7,374,534 B2 | 5/2008 | Dalton |
| 7,473,222 B2 | 1/2009 | Dewey et al. |
| 7,758,501 B2 | 7/2010 | Frasier et al. |
| 7,887,482 B2 | 2/2011 | Hamada |
| 7,935,053 B2 | 5/2011 | Karpowicz et al. |
| 7,981,031 B2 | 7/2011 | Frasier et al. |
| 7,985,179 B2 | 7/2011 | Gephart et al. |
| 8,007,492 B2 | 8/2011 | DiPoto et al. |
| 8,267,859 B2 | 9/2012 | Holmes |
| 2003/0095781 A1* | 5/2003 | Williams ............ 385/146 |
| 2006/0206008 A1* | 9/2006 | Dalton ............... 600/215 |
| 2007/0238932 A1 | 10/2007 | Jones et al. |
| 2009/0018400 A1 | 1/2009 | Raymond et al. |
| 2010/0240961 A1* | 9/2010 | Aferzon ............. 600/212 |
| 2011/0015491 A1 | 1/2011 | Ravikumar et al. |
| 2011/0060183 A1 | 3/2011 | Castro et al. |
| 2011/0208008 A1 | 8/2011 | Michaeli et al. |
| 2012/0215070 A1* | 8/2012 | Kahle et al. ........ 600/208 |
| 2013/0197313 A1* | 8/2013 | Wan .................. 600/202 |
| 2014/0114135 A1* | 4/2014 | Ellman ............... 600/214 |

* cited by examiner

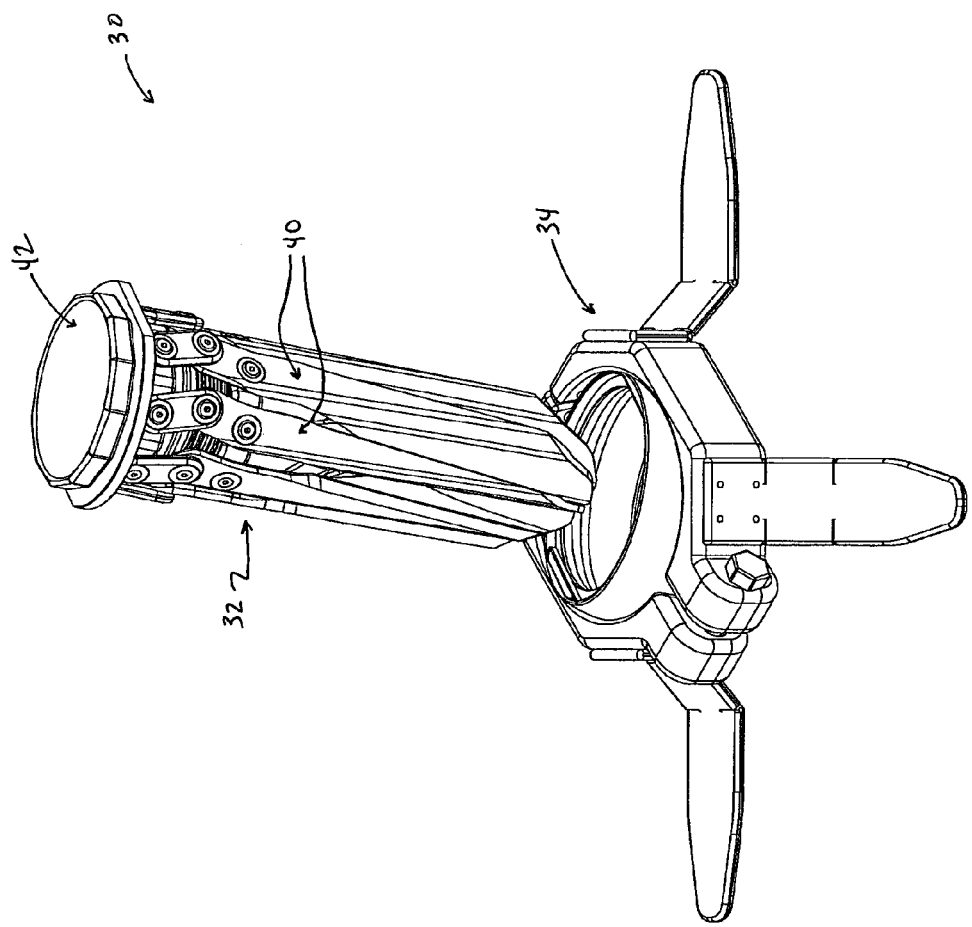

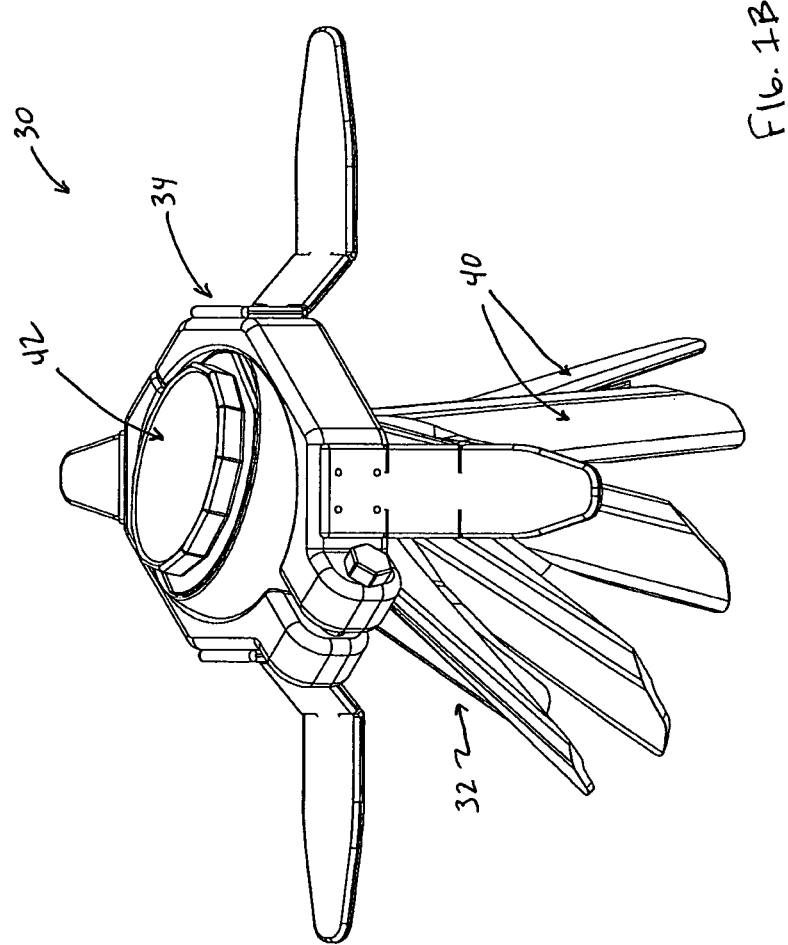

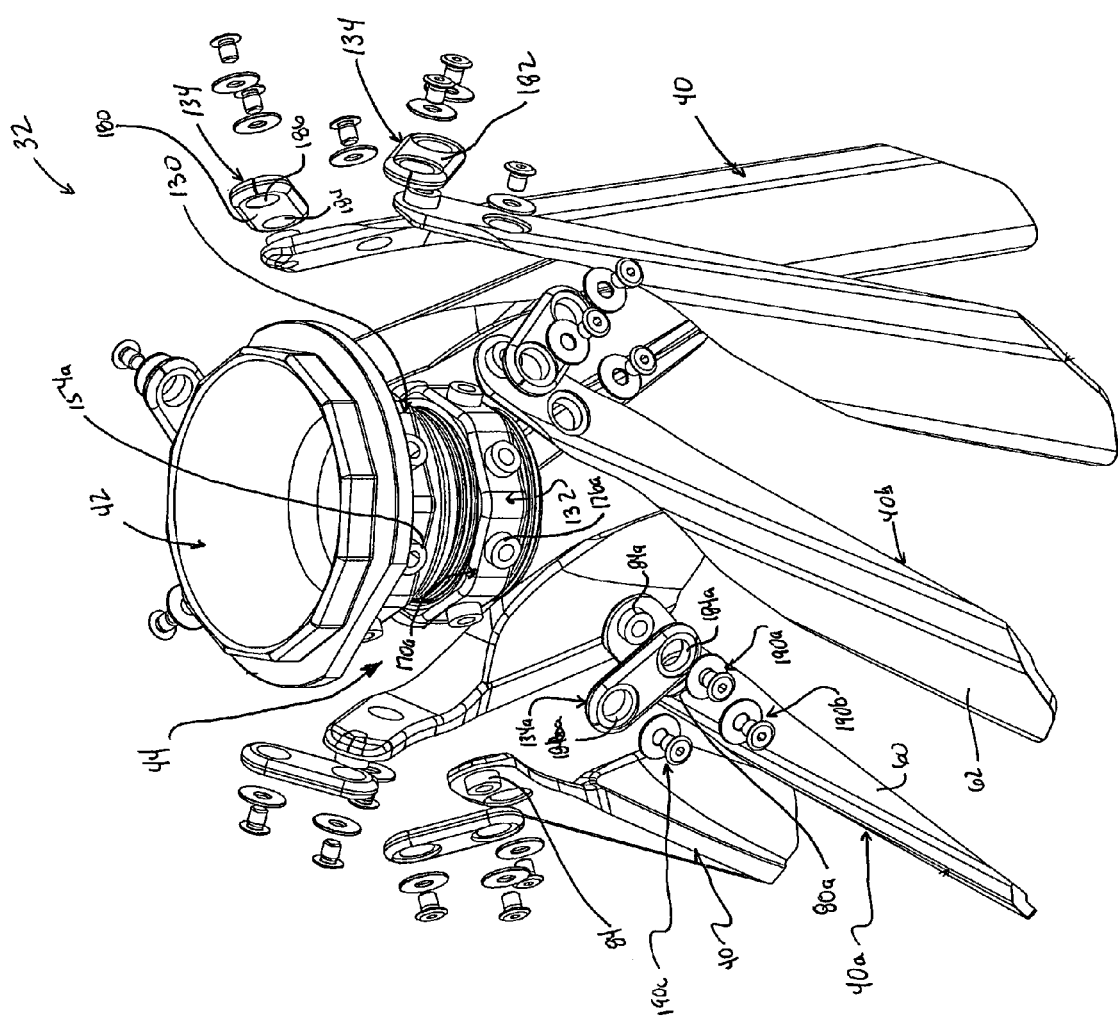

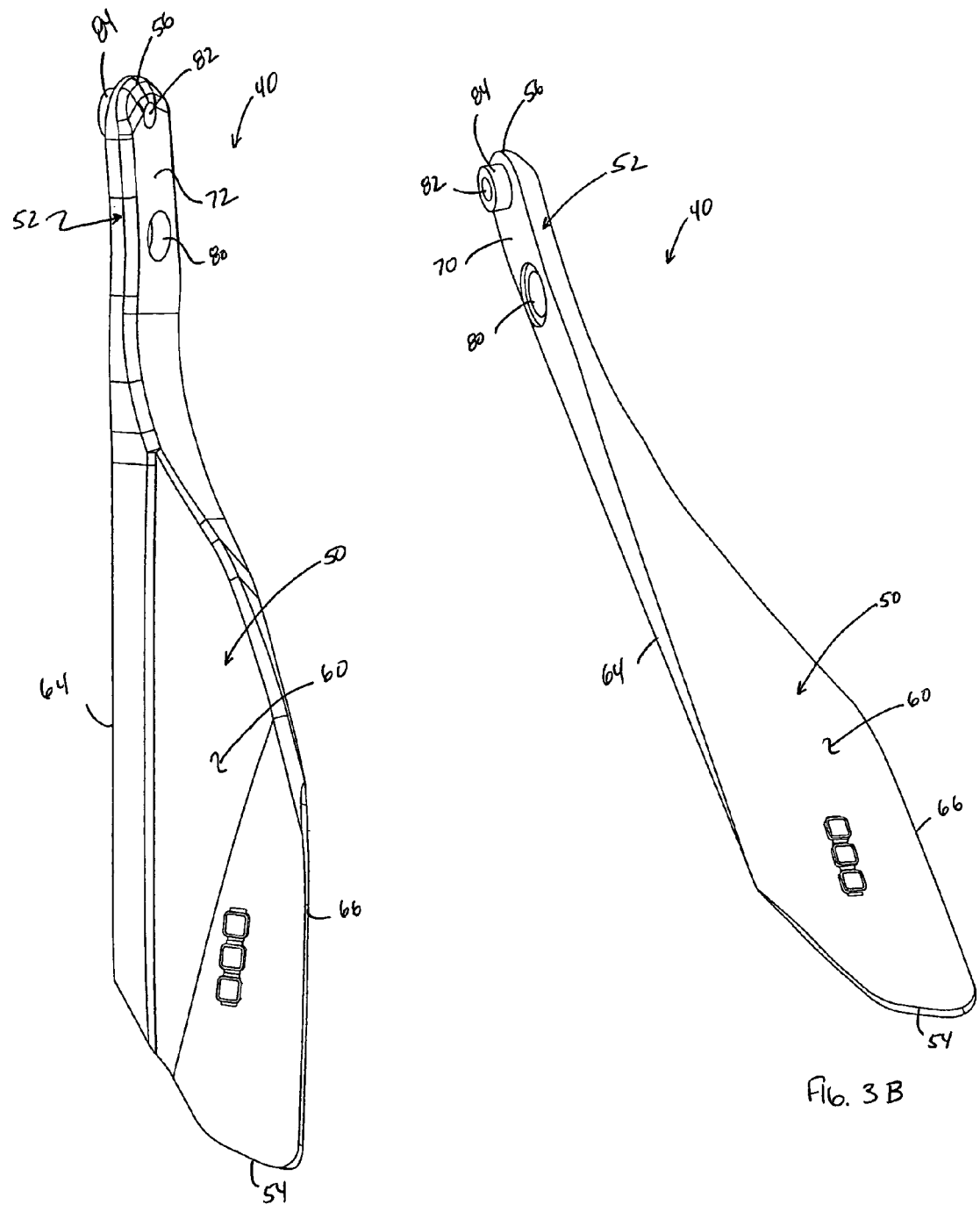

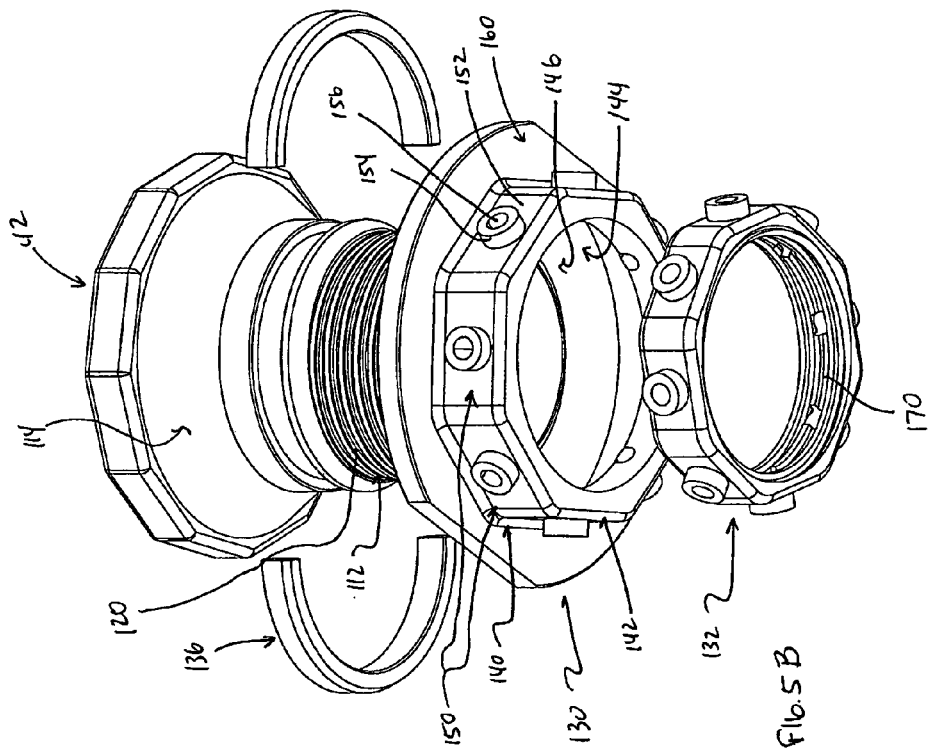
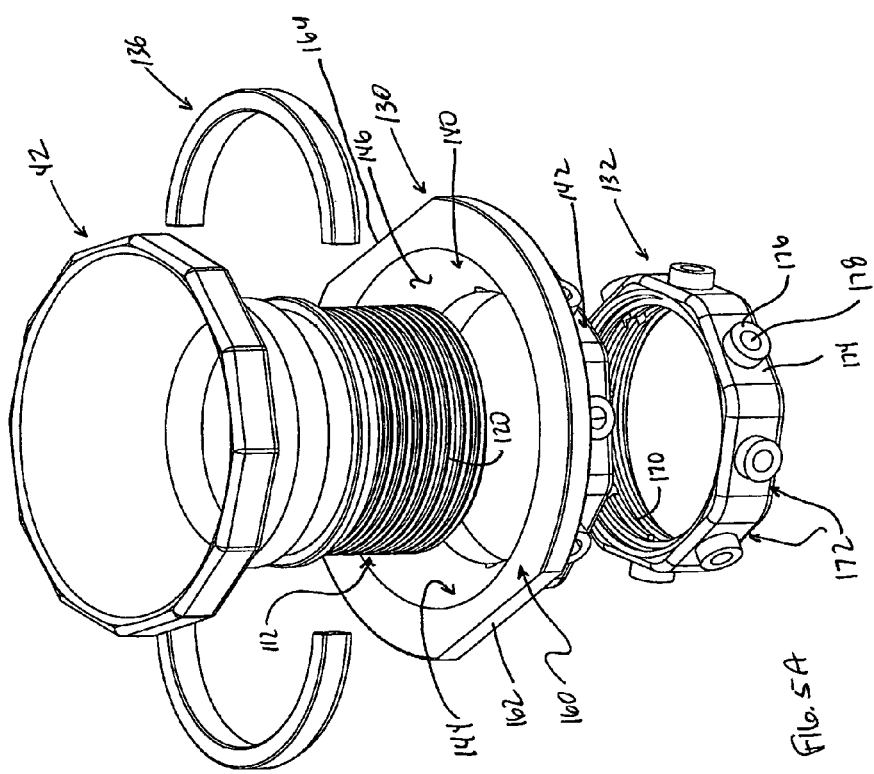

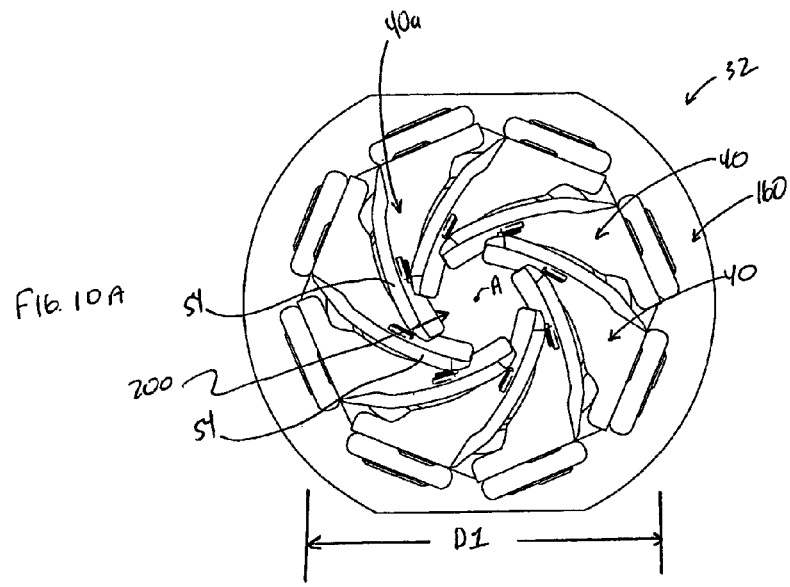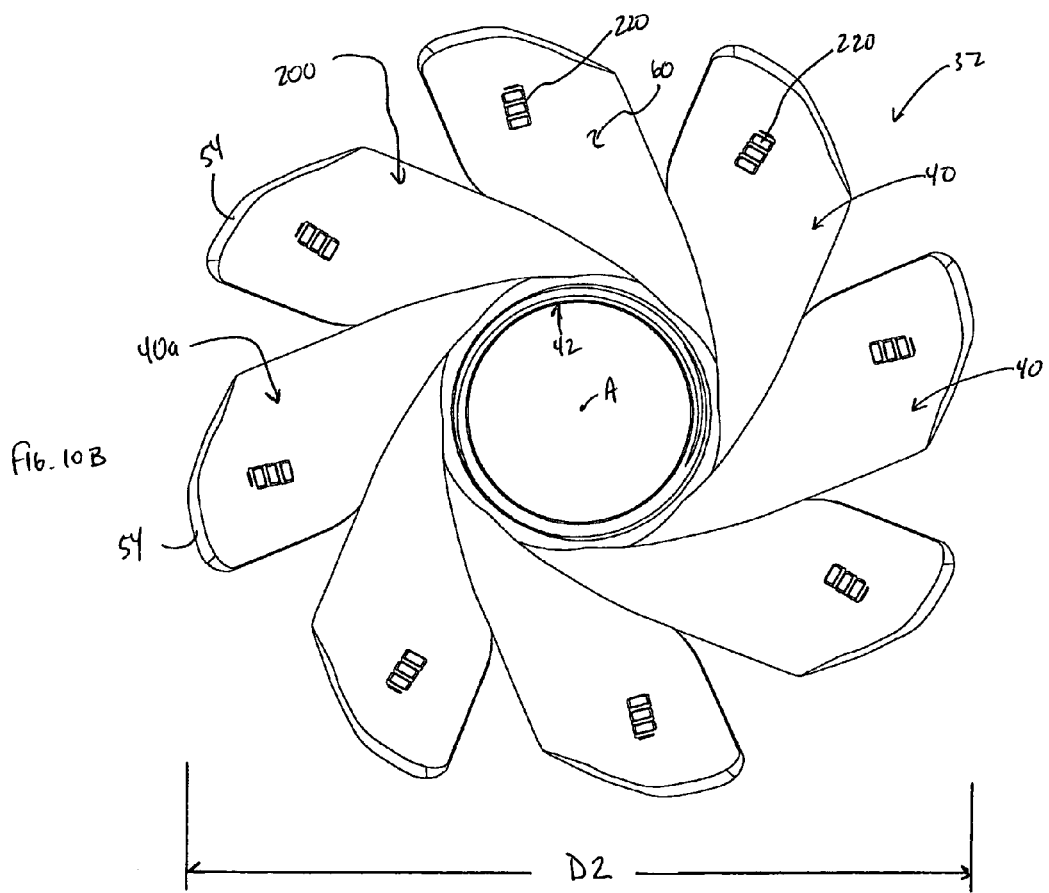

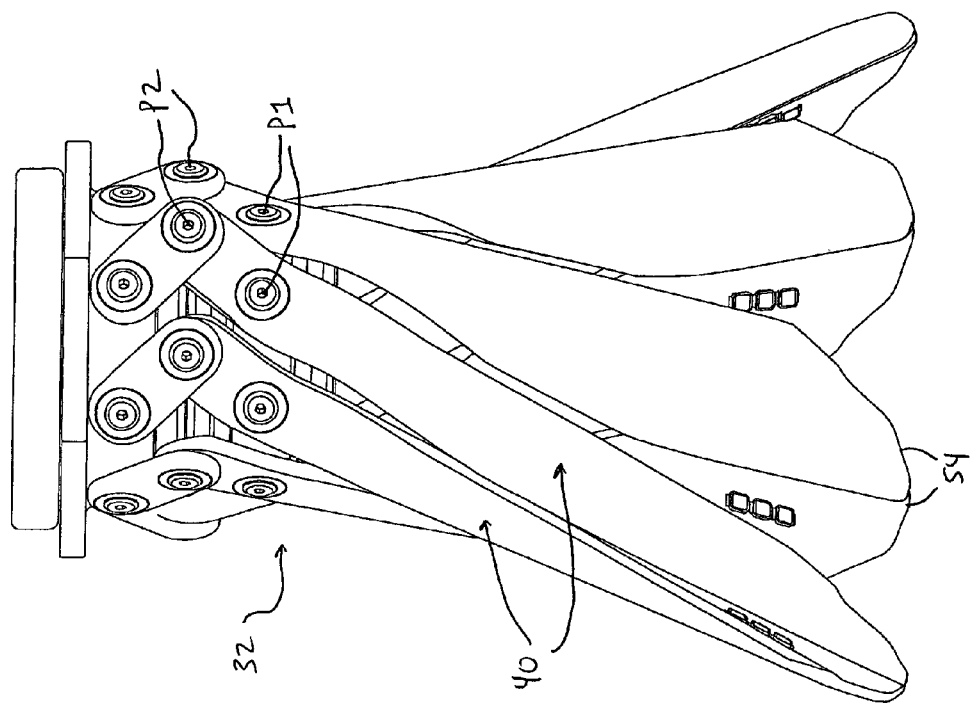
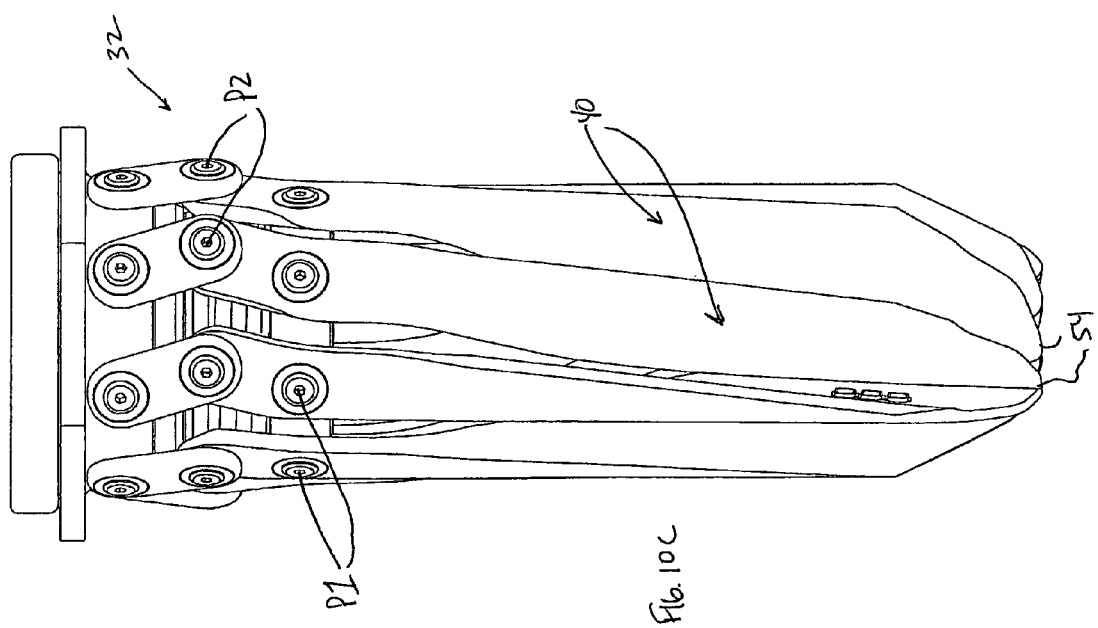

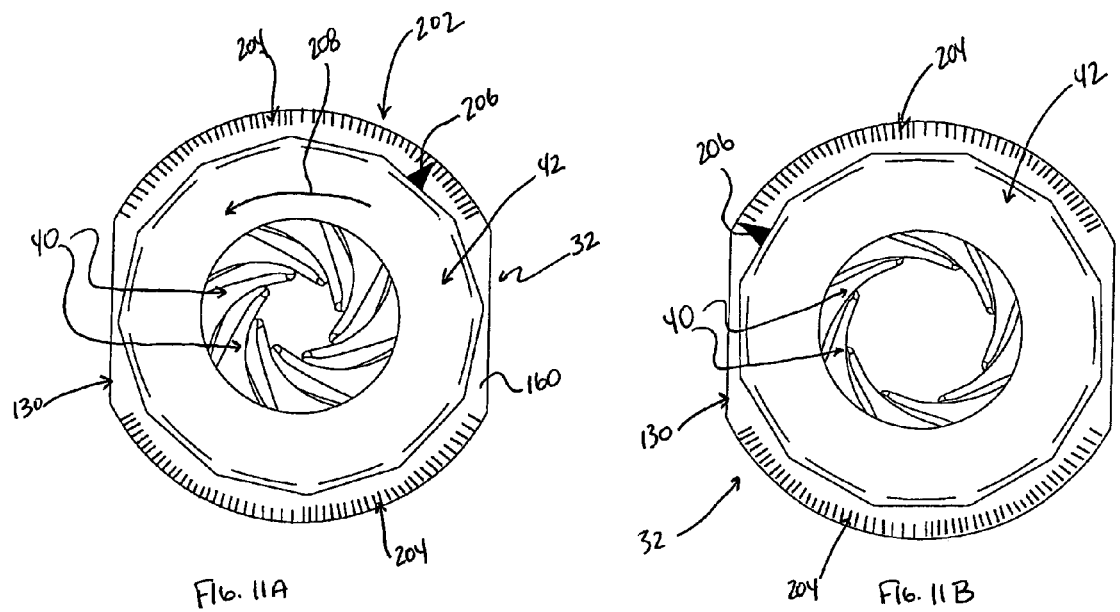
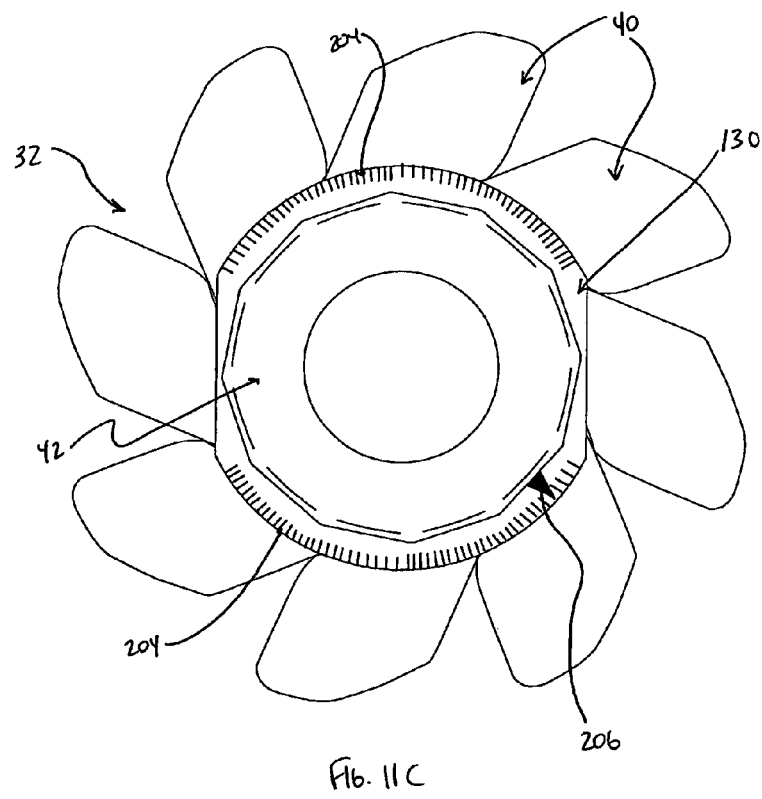
FIG. 11A
FIG. 11B
FIG. 11C

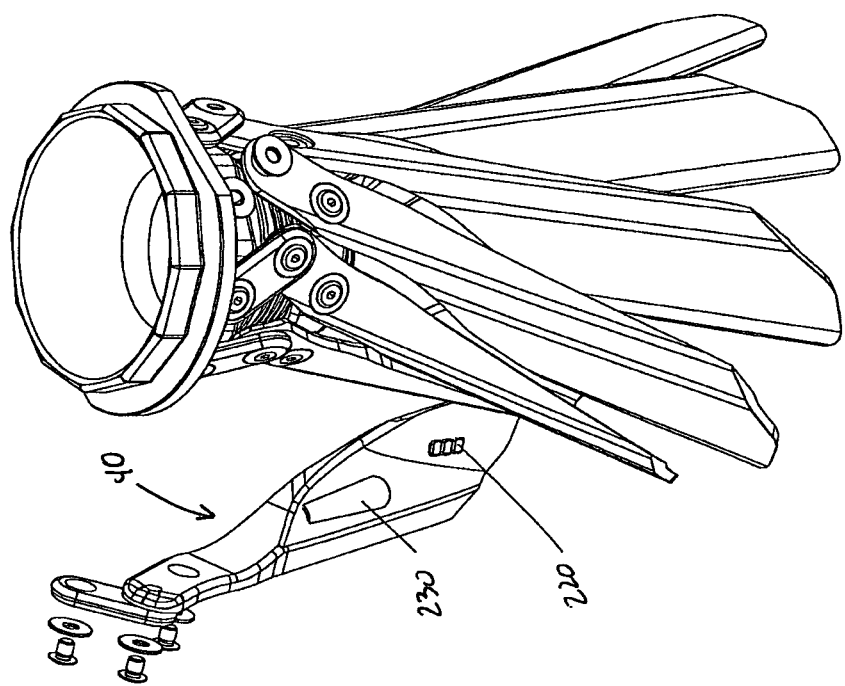

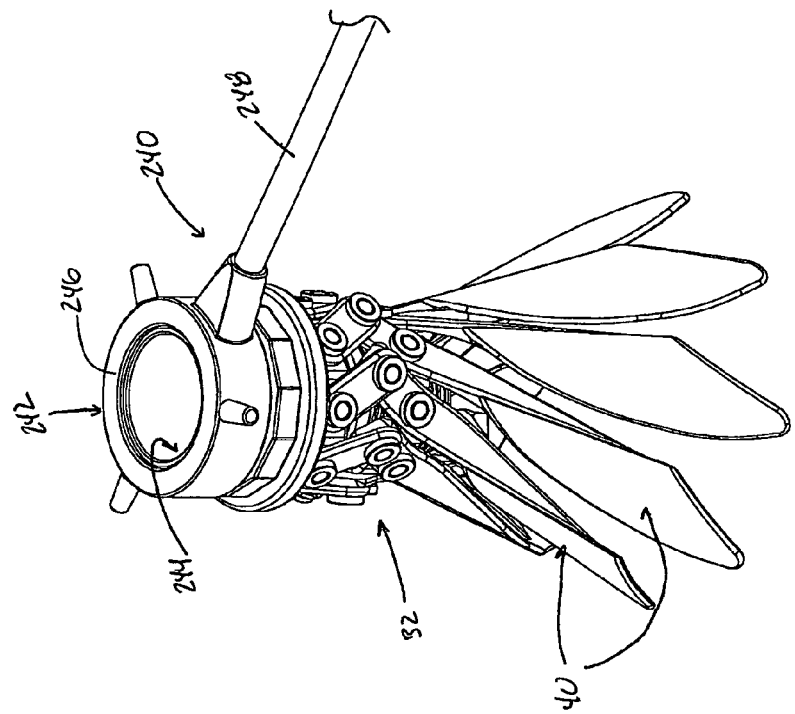
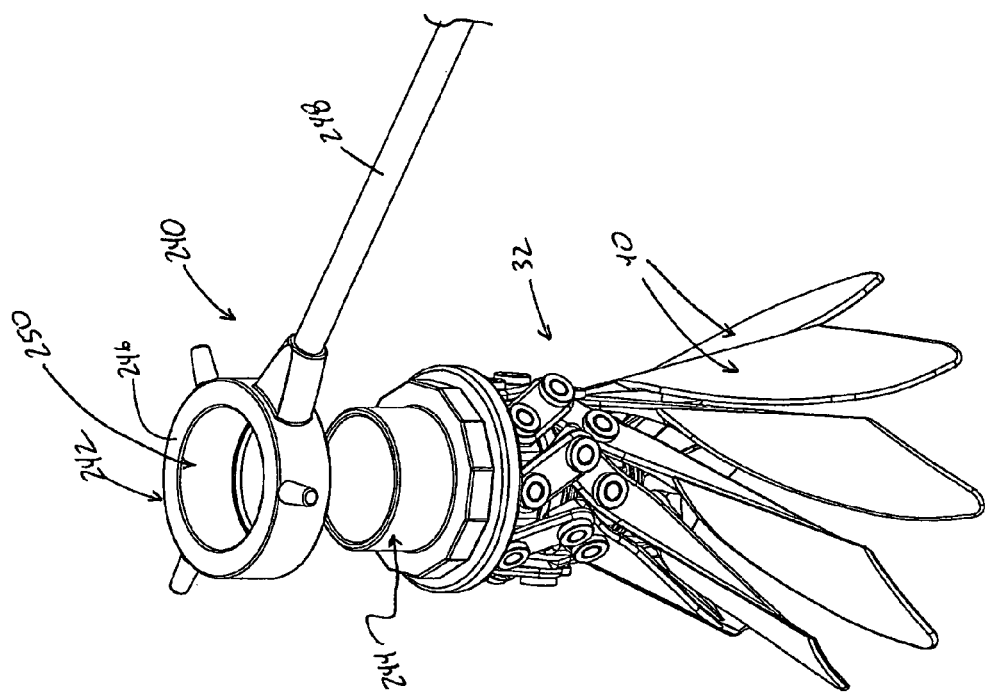

MICRO-ORIFICE SURGICAL ACCESS SYSTEM

BACKGROUND

The present disclosure relates to surgical access systems. More particularly, it relates to systems serving as both an access port and retractor to facilitate performance of surgical procedures through an incision (or other opening), for example procedures performed in the abdominal cavity.

Surgical procedures for pathologies located deep within the body are conventionally performed on either an open surgical basis or via a minimally invasive approach. Both techniques typically require general anesthesia. With open surgery, a relatively long incision is formed through the skin and then spread apart or retracted to afford the surgeon access to tissue, organs, and other anatomy beneath the skin. These open surgery procedures can be highly traumatic to the patient, and often have a lengthy and painful post-operative recovery. Moreover, the substantial incision required to perform the procedure invariably results in a major scar.

Minimally invasive techniques (e.g., minimally invasive laparoscopic surgery or MILS) overcome many of the above concerns whereby one (or more) relatively small incisions are made through the skin, and endoscopic surgical tools inserted through the incision(s). Because the procedure is performed deep beneath the skin, a camera or other visualization device must be employed, meaning that the surgeon has only an indirect and/or two-dimensional view of the surgical field. The surgical tools utilized with minimally invasive procedures are uniquely formatted for manipulation through a small, enclosed access port and are thus complex and expensive. From a patient recovery perspective, it is desirable that only a single incision be made, and is often referred to as a "single port" minimally invasive procedure. Existing single port technology includes single port access (SPA) surgery (also known as laparo endoscopic single-site surgery (LESS)), single incision laparoscopic surgery (SILS), one port umbilical surgery (OPUS), single port incisionless conventional equipment-utilizing surgery (SPICES), natural orifice transumbilical surgery (NOTUS), and embryonic natural orifice transumbilical surgery (E-NOTES). Each approach is a surgically advanced procedure in which the surgeon operates almost exclusively through a single entry point, typically the patient's navel. These surgical procedures generally require the patient to be under general anesthesia, intubated and insufflated under laparoscopic visualization. Further, retraction to obtain visualization is generally achieved using an alternate point of entry.

Bariatric surgeries (e.g., gastric banding, gastric bypass, etc.) and other procedures in the abdominal cavity are but one example of a surgical scenario in which an open and or a minimally invasive technique can be employed. With the open surgical approach, an incision on the order of 20 cm (or more) is necessary to obtain surgical access. The trauma associated with this incision and corresponding retraction is significant. Conversely, with the laparoscopic approach, carbon dioxide insufflation of the abdomen is required, and multiple (though small) incisions are made to deploy all of the required endoscopic instrumentation. The port device(s) through which the instruments are inserted must maintain an air tight seal over the corresponding incision to ensure viability of the insufflation. Moreover, the caregiver setting in which the procedure is performed must have all of the expensive endoscopic instruments on hand.

In light of the above, conventional surgical procedures require the use of general anesthesia. Open surgery is highly traumatic to the patient. Minimally invasive procedures require an expensive laparoscopy platform (costing caregiver institutions millions of dollars) and as a result, are oftentimes simply not available to many patients. Therefore, a need exists for a surgical access system that is relatively inexpensive yet minimizes patient trauma, and meets three primary needs of the surgical setting: access, retraction and visualization.

SUMMARY

Some aspects of the present disclosure relate to a surgical access system for intra-abdominal and other surgical procedures (e.g., abdominal cavity procedures), facilitating introduction of surgical tools to the surgical field via a single incision along with retraction of tissue, organs, etc., within the surgical field. The surgical access system includes an access port device. The access port device has a port member, a plurality of blades, and an articulation mechanism. The port member defines a central passageway extending along a longitudinal axis and through which surgical instruments can be introduced. The plurality of blades are circumferentially arranged about the longitudinal axis to collectively define an access region open to and extending distally from the central passageway. Each of the blades terminates at a tip opposite the port member. The articulation mechanism is configured to define a first pivot point along a length of each of the blades. The articulation mechanism is operable to articulate the blades through a collapsed state and an expanded state. The tips collectively define a first diameter in the collapsed state and a second diameter in the expanded state. The second diameter is greater than the first diameter. Further, the articulation mechanism is configured such that the blades rotate about the corresponding first pivot point, and the first pivot points collectively move longitudinally relative to the port member in transitioning between the contracted and expanded states. With this configuration, the port access device can be inserted through a relatively short incision (with the blades in the contracted stated) and can effectuate a relatively significant expansion of the surgical field (e.g., retraction of tissue, organs, etc.) as the blades transition toward the expanded state. Thus, use of the port access device is significantly less traumatic to the patient as compared to conventional open surgery techniques, and is substantially less expensive and complex than laparoscopic-based procedures.

In some embodiments, the articulation mechanism is configured to effectuate transitioning between the collapsed and expanded states in response to user-prompted rotation of the port member. For example, the articulation mechanism can establish two pivot points along the length of each of the blades, and interconnects the blades with the port member via a drive collar commonly coupled to the blades and a plurality of links, respective ones of which are coupled to a corresponding one of the blades. The pivot points are each caused to move longitudinally with rotation of the port member, allowing the blade to pivot or rotate about the corresponding pivot points.

Other aspects of the present disclosure relate to an anchoring device useful with the surgical access system. The anchoring device includes a receiving apparatus and a plurality of platforms. The receiving apparatus defines a central aperture through which the blades (in the collapsed stated) can be inserted. Further, the receiving apparatus is configured to selectively hold a portion of the port access device proximal the blades, and in some embodiments establishes a ball joint-type mounting whereby the held port access device can be spatially rotated. An optional locking mechanism provided with the anchoring device selectively locks the port access device at a desired spatial orientation. The platforms extend from the receiving apparatus, and are configured to secure or otherwise support the anchoring device (and thus the held port access device) relative to the patient.

In some embodiments, the surgical access systems of the present disclosure include one or more lighting devices for illuminating the surgical field. For example, LEDs or similar light sources can be carried by one or more of the blades. Alternatively, a light ring configured for mounting to the port access device can be provided. In other embodiments, surgical field illumination is accomplished by transillumination of a glass or plastic tube passing through the incision; an illumination source is associated with the tube outside of the patient, with the tube directing the light into the surgical field to illuminate an interior of the tube and the surgical field.

BRIEF DESCRIPTION OF THE DRAWINGS

FIG. 1A is a perspective view of a surgical access system in accordance with principles of the present disclosure, and including a port access device and an anchoring device;

FIG. 1B is a perspective view of the surgical access system of FIG. 1A and illustrating the port access device assembled to the anchoring device;

FIG. 2 is an exploded view of a port access device useful with the system of FIG. 1;

FIGS. 3A and 3B are perspective views of a blade component useful with the port access device of FIG. 2;

FIGS. 5A and 5B are perspective views of portions of an articulation mechanism useful with the port access device of FIG. 2 and including the port member of FIG. 4A;

FIG. 10A is an end view of the port access device of FIG. 2 upon final assembly and illustrating the blades in a contracted state;

FIG. 10B is the end view of FIG. 10A and illustrating the blades in an expanded state;

FIG. 10C is a side view of the port access device of FIG. 2 upon final assembly and illustrating the blades in a contracted state;

FIG. 10D is the side view of FIG. 10C and illustrating the blades in an expanded state;

FIG. 11A is a top view of a portion of another surgical access system in accordance with principles of the present disclosure;

FIGS. 11B and 11C are top view illustrating use of the system of FIG. 11A;

FIG. 13 is a perspective view of another port access device in accordance with principles of the present disclosure and including an alternative blade;

FIG. 14A is a perspective view of another surgical access system in accordance with principles of the present disclosure, and including a port access device and a light source;

FIG. 14B is the perspective view of FIG. 14A and illustrating the light source assembled to the port access device;

DETAILED DESCRIPTION

System Overview

Figure 3C:
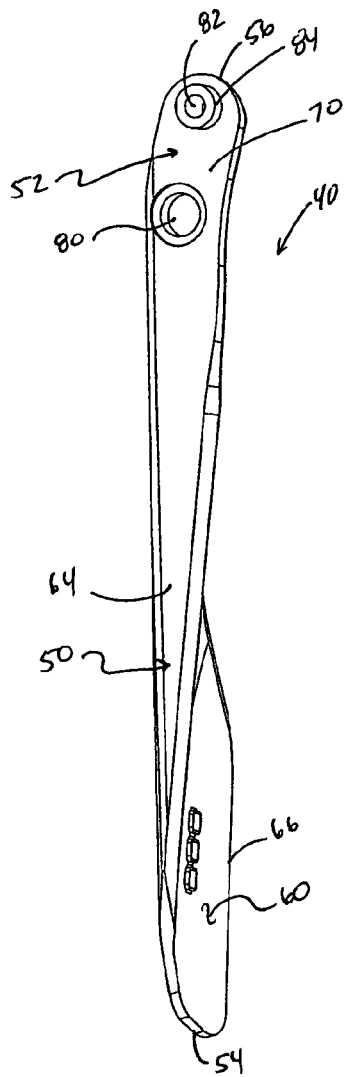
FIGS. 3C and 3D are opposing side views of the blade of FIG. 3A.
Figure 3D:
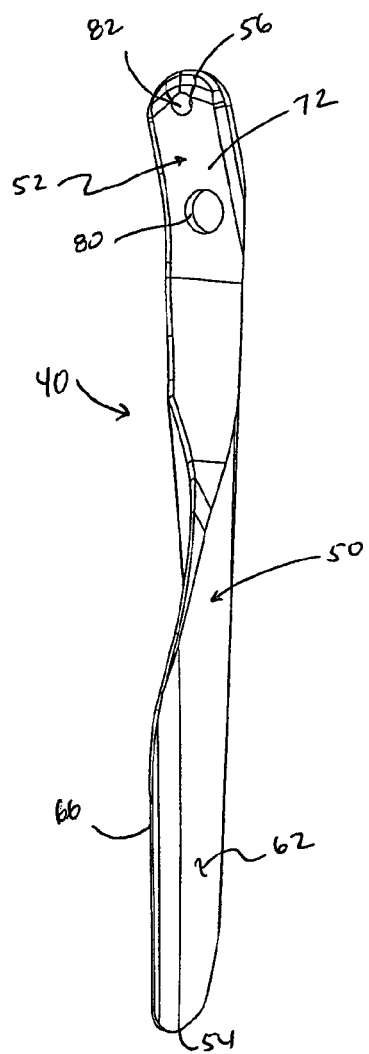
Figure 3E:
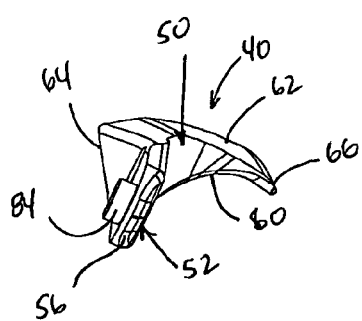
FIG. 3E is an end view of the blade of FIG. 3A.

One embodiment of a surgical access system 30 in accordance with principles of the present disclosure is shown in FIGS. 1A and 1B. The system 30 includes a port access device 32 and an anchoring device 34. The devices 32, 34 are described in greater detail below. In general terms, however, the port access device 32 includes a plurality of blades 40 and a port member 42. The port access device 32 is operable to collectively transition the blades 40 between a first, contracted state (FIG. 1A) and a second, expanded state (FIG. 1B). The anchoring device 34 is configured to receive the port access device 32 with the blades 40 in the contracted state, and serves to stabilize the port access device 32 relative to a patient (not shown). Transitioning of the blades 40 to or toward the expanded state retracts contacted subcutaneous tissue, organs, etc., at the surgical field. With this construction, the system 30 is highly useful with a plethora of percutaneous surgical procedures, with the port access device 32 providing surgical tool access (and direct visualization) through a relatively small incision, along with desired subcutaneous tissue refraction. The anchoring device 34 serves to support the port access device 32 external the patient, optionally permitting spatial rotation of the port access device 32 relative to the patient. Optional lighting devices (not shown) enhance visibility in the surgical field established by the port access device 32. Procedures utilizing the systems 30 of the present disclosure are significantly less traumatic to the patient as compared to conventional open surgery techniques, and are highly cost-effective.

Port Access Device 32

The port access device 32 is shown in greater detail in FIG. 2 and in some embodiments includes the plurality of blades 40, the port member 42, and an articulation mechanism 44 (referenced generally). The blades 40 are arranged in a circumferential pattern about the port member 42. The articulation mechanism 44 connects the plurality of blades 40 with the port member 42, and is operable to effectuate transitioning of the blades 40 between the contracted (FIG. 1A) and expanded (FIG. 1B) states. In some embodiments, the articulation mechanism 44 is configured such that user-prompted rotation of the port member 42 effectuates transitioning of the blades 40.

In some embodiments, the blades 40 are identical, and are sized and shaped to compactly overlap one another in the contracted state (FIG. 1A) and transition between the contracted and expanded (FIG. 1B) states in a non-interfering manner. While the port access device 32 is illustrated as including eight of the blades 40, any other number, either greater or lesser, is envisioned. In some embodiments, the port access device 32 includes at least six of the blades 40 equidistantly arranged about the port member 42.

One of the blades 40 is shown in greater detail in FIGS. 3A-3E, and generally defines a blade body 50 and a shaft 52. The blade body 50 extends from the shaft 52 and terminates at a tip 54. The shaft 52 forms a coupling end 56 opposite the tip 54. The blade body 50 expands in width in extension from the shaft 52, and defines opposing, first and second major surfaces 60, 62. Relative to an arrangement of the blade 40 upon final assembly of the port access device 32 (e.g., as identified in FIG. 2), the first major surface 60 is interiorly facing, whereas the second major surface 62 serves as an exterior surface. With these designations in mind, the interior and exterior surfaces 60, 62 exhibit corresponding curvatures that promote a non-interfering interface between the interior surface 60 and the exterior surface 62 of two, circumferentially adjacent ones of the blades 40 (e.g., for the circumferentially adjacent blades 40a, 40b identified in FIG. 2, the interior surface 60 of the first blade 40a can overlap the exterior surface 62 of the second blade 40b as described below). For example and returning to FIGS. 3A-3E, the interior surface 60 can exhibit a slightly concave shape, whereas the exterior surface 62 can have a slightly convex shape. The non-interfering interface between circumferentially adjacent blades 40 can be further enhanced by an optional tapering thickness along the blade body 50 from a trailing side 64 to a leading side 66.

The shaft 52 is arranged as an extension from the trailing side 64 of the blade body 50 (e.g., generally in a plane of the trailing side 64). A thickness of the shaft 52 is greater than that of the blade body 50 (at least relative to a thickness at the leading side 66) and forms opposing, first and second engagement faces 70, 72. The engagement faces 70, 72 can be substantially flat (e.g., within 10% of a truly flat surface) and substantially parallel (e.g., within 10% of a truly parallel arrangement). As reflected in FIGS. 3A-3E, the engagement faces 70, 72 are non-parallel relative to a major plane generally defined by the blade body 50, and in some embodiments are substantially perpendicular to the blade body 50. Stated otherwise, while the blade body 50 exhibits some curvature along the interior and exterior surfaces 60, 62 in extension from a plane of the second engagement face 72 to the leading side 66, a major plane is generally defined by the blade body 50 extending through the trailing and leading sides 64, 66 that is substantially perpendicular or orthogonal (e.g., within 10% of truly perpendicular relationship) to a plane of the second engagement face 72, and laterally off-sets the leading edge 66 from the shaft 52.

The engagement faces 70, 72 are configured to promote coupling to, and a sliding-type interface with, other components of the port access device 32 (FIG. 2). In this regard, first and second bores 80, 82 are formed through the shaft 52, and are each open to the first and second engagement faces 70, 72.

The second bore 82 is defined adjacent the coupling end 56, whereas the first bore 80 is defined between the second bore 82 and the blade body 50. As described in greater detail below, the bores 80, 82 facilitate a rotatable coupling with other components of the port access device 32 and thus effectively serve as "part" of the articulation mechanism 44 (FIG. 1A). In some embodiments, a support ring 84 is optionally formed at the second bore 82 that promotes the rotatable mounting described below. A similar structure can be provided with the second bore 80. In other embodiments, the support ring 84 is omitted.

Figure 4A:
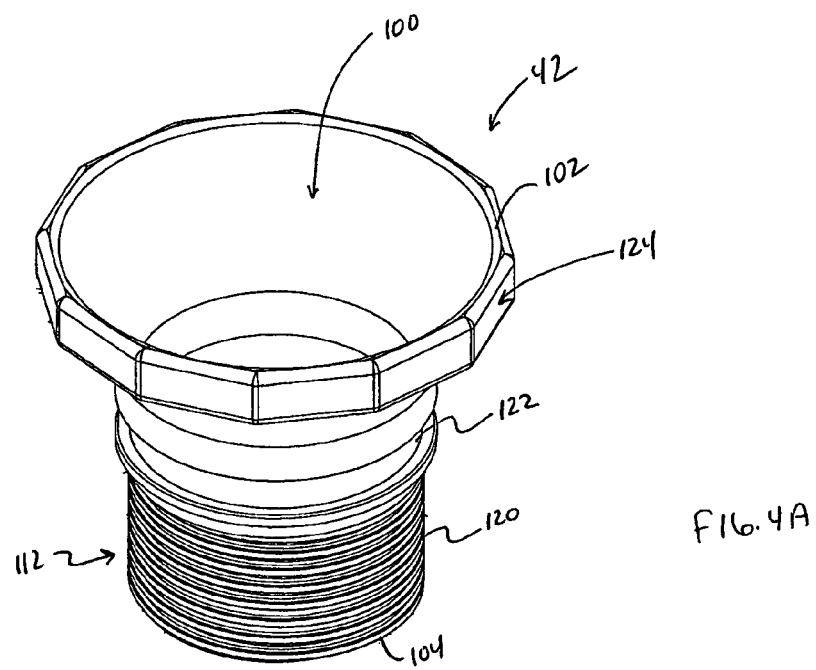
FIG. 4A is a perspective view of a port member useful with the port access device of FIG. 2.
Figure 4B:
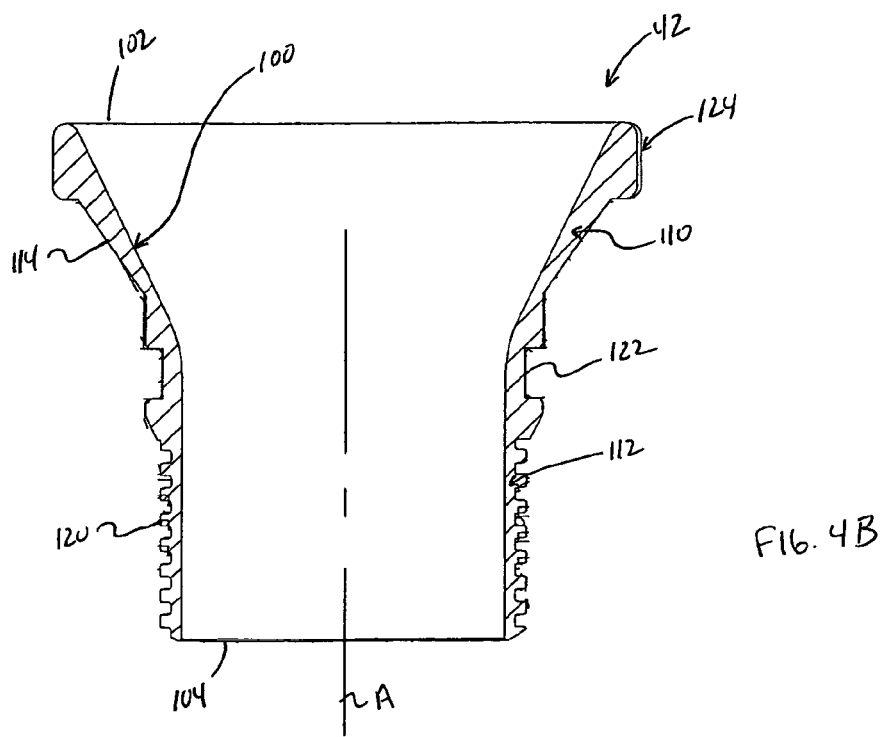
FIG. 4B is a cross-sectional view of the port member of FIG. 4A.

Returning to FIG. 2, the port member 42 is configured for assembly with the articulation mechanism 44. With this in mind, FIGS. 4A and 4B illustrate the port member 42 in greater detail. The port member 42 is cylindrical, having a generally funnel-like shape defining a central passageway 100 extending between (and open relative to) opposing, top (or proximal) and bottom (or distal) ends 102, 104. As best shown in FIG. 4B, the central passageway 100 can taper in diameter from the proximal end 102 along a proximal region 110 thereof, and has a relatively uniform diameter along a distal region 112. An outer surface 114 of the proximal region 110 is relatively smooth, and can have the same tapering diameter shape as the central passageway 100. A size of the port member 42 (and thus of the central passageway 100) can vary as a function of the intended end-use procedure, but is generally sized and shaped to receive various surgical instruments there through. For reasons made clear below, the cylindrical format of the port member 42 can be viewed as defining a circumference about a central longitudinal axis A. Assembly and manipulation of the port access device 32 (FIG. 2) can be described relative to the port member 42 circumference and the central longitudinal axis A, and reference to the "longitudinal direction" throughout the present disclosure means along or parallel with the central longitudinal axis A.

In some embodiments, the port member 42 includes various features that facilitate assembly of the port access device 32 (FIG. 2). For example, exterior threads 120 are formed along the distal region 112, and a circumferential slot 122 is formed between the proximal and distal region 110, 112. The threads 120 and the slot 122 interface with various components of the articulation mechanism 44 as described below. Additionally, the port member 42 can form a gripping surface 124 at the proximal end 102 configured to promote user grasping and manipulation of the port member 42. For example, the gripping surface 124 can include a series of corners interposed between flattened regions. Regardless, where provided, the gripping surface 124 readily assists a user in rotating the port member 42 (about the central axis A).

Returning to FIG. 2, the articulation mechanism 44 can assume a variety of forms and in some embodiments includes a hub 130, a drive collar 132, and a plurality of links 134. In general terms, the hub 130 rotatably receives the port member 42. The drive collar 132 is threadably coupled to the port member 42, and is rotatably coupled to each of the blades 40. Finally, the links 134 rotatably connect each of the blades 40 with the hub 130.

The hub 130 and drive collar 132 are shown in greater detail in FIGS. 5A and 5B, along with the port member 42. An additional, optional stopper 136 component of the articulation mechanism 44 is also illustrated.

The hub 130 is a generally cylindrical body, defining a bearing section 140 and a hub body 142. A central passage 144 (referenced generally) extends through the hub 130. In this regard, the central passage 144 is defined along the bearing section 140 by a bearing surface 146 that is sized and shaped in accordance with the tapering shape of the port member outer surface 114. With this construction, upon nested assembly of the port member 42 with the hub 130, the port member outer surface 114 abuts the bearing surface 146 in a manner that permits the port member 42 to rotate relative to the hub 130 about the central axis A (FIG. 4B) with minimal frictional interference. For example, a sliding, bearing-type interface is established between the port member outer surface 114 and the bearing surface 146.

The hub body 142 projects distally from the bearing section 140. A diameter of the central passage 144 along the hub body 142 is sized to receive (i.e., is slightly larger than) an outer diameter of the port member distal region 112. As best shown in FIG. 5B, a plurality of circumferentially aligned coupling zones 150 are formed along an exterior of the hub body 142, each including a platform 152 and a support ring 154. The platform 152 is substantially flat (e.g., within 10% of a truly flat surface). The support ring 154 projects from the platform 152 and defines a hole 156. As described below, the support ring 154 is configured to promote a rotatable coupling with one of the links 134 (FIG. 2), with the platform 152 interfacing with the corresponding link 134 in a manner dictating planar motion. The coupling zones 150 can assume other forms as a function of the articulation mechanism 44 (FIG. 2) design. Regardless, the number of coupling zones 150 corresponds with the number of the links 134.

In some embodiments, the hub 130 further includes or forms an optional flange 160. The flange 160 projects radially outwardly from the bearing section 140 opposite the hub body 142 and is configured to interface with the anchoring device 34 (FIG. 1A) as described below. For example, in some embodiments, the flange 160 forms opposing side edges 162, 164 that are substantially flat or linear, whereas a remainder of a perimeter of the flange 160 is curved. The flange 160 can alternatively have other shapes and sizes, and in other embodiments can be provided apart from the hub 130 (e.g., the port member 42 can form a flange or other feature configured to interface with the anchoring device 34; an additional component apart from the port member 42 and the hub 130 can form the flange 160; etc.).

The drive collar 132 is a ring-shaped body configured for threadable engagement with the outer threads 120 of the port member 42 (e.g., via an interiorly threaded surface 170). A plurality of circumferentially aligned coupling regions 172 are formed along an exterior surface of the drive collar 132. The coupling regions 172 can be akin to the coupling regions 150 described above, and each includes a base 174 and a support ring 176. The base 174 is substantially flat (e.g., within 10% of a truly flat surface). The support ring 176 projects from the base 174 and defines a hole 178. As described below, the support ring 176 is configured to promote a rotatable coupling with one of the blades 40 (FIG. 2), with the base 174 interfacing with the corresponding blade 40 in a manner dictating planar motion. The coupling regions 172 can assume other forms as a function of the articulation mechanism 44 (FIG. 2) and/or blade 40 design. Regardless, the number of coupling regions 172 corresponds with the number of blades 40.

Returning to FIG. 2, the links 134 are configured to connect respective ones of the blades 40 with the hub 130. Thus, the number of links 134 corresponds with the number of blades 40 (e.g., in some embodiments, one link 134 is provided for each one of the blades 40). Each link 134 has opposing major faces 180, 182 that are substantially flat (e.g., within 10% of a truly flat surface), and defines first and second holes 184, 186 through a thickness thereof. The links 134 can be identical, having a length selected in accordance with a desired range of motion of the blades 40 (e.g., overall length of the link 134, a linear distance between centerlines of the holes 184, 186, etc.). The holes 184, 186 are sized in accordance with the support ring 84 of each of the blades 40 and the support rings 154 of the hub 130, respectively.

Figure 6:
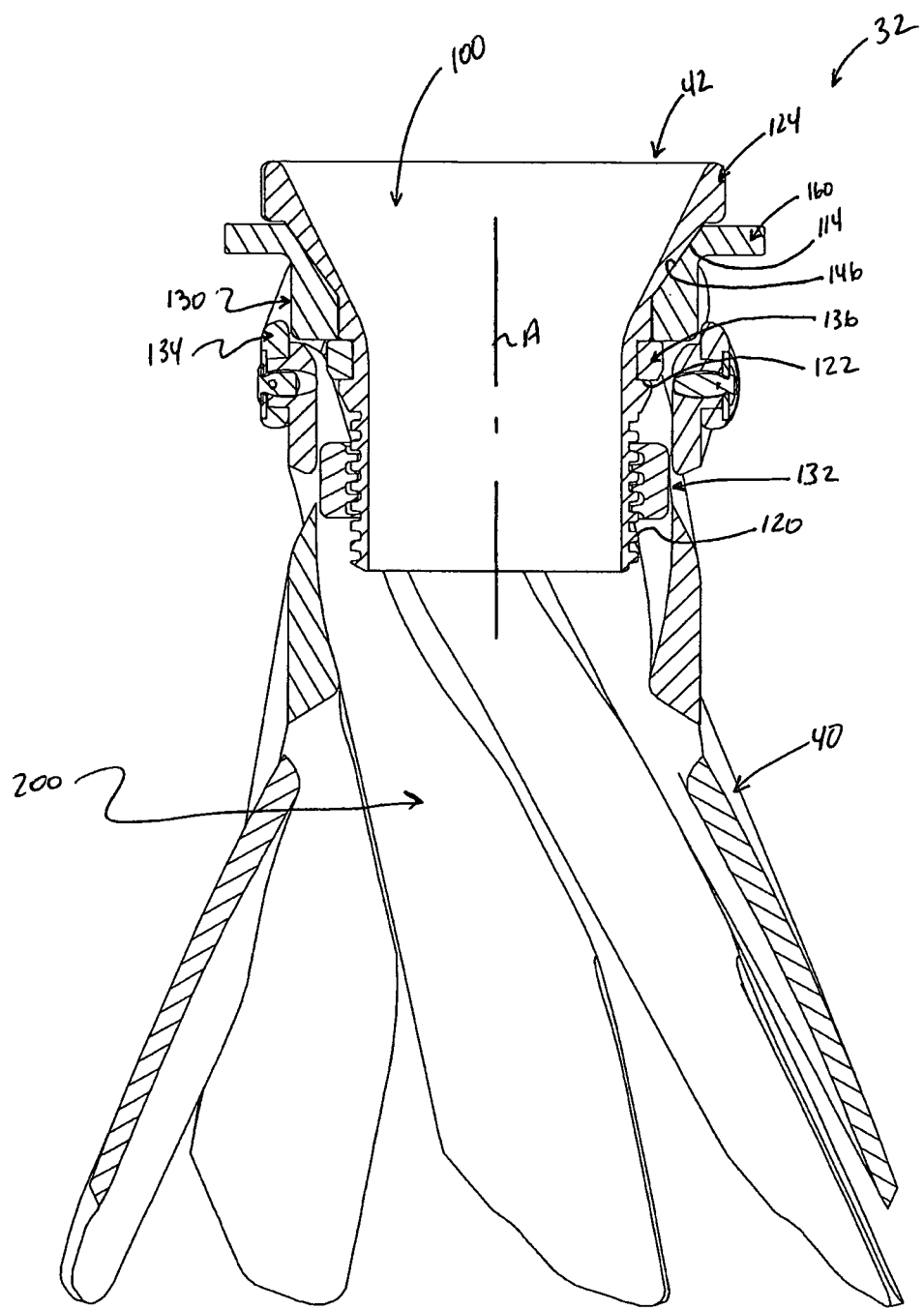
FIG. 6 is a cross-sectional view of the port access device of FIG. 2 upon final assembly and in an expanded state.

With reference between FIGS. 2, 5A and 6, assembly of the port access device 32 includes nesting the port member 42 within the hub 130, with the outer surface 114 of the port member 42 abutting the bearing surface 146 of the hub 130. The flange 160 is located adjacent the gripping surface 124, and projects radially beyond the port member 42. The hub 130 can be rotatably captured relative to the port member 42 in various fashions. For example, the stopper 136 (e.g., a split ring) is assembled within the slot 122 of the port member 42 and abuts against a bottom end of the hub 130; an upper end of the hub 130 bears against an underside of the gripping surface 124. Regardless, while the port member 42 and the hub 130 are longitudinally coupled to one another, the port member 42 can rotate relative to the hub 130 (about the central axis A). The drive collar 132 is then threaded on to the threads 120 of the port member 42.

Respective ones of the blades 40 are assembled to corresponding ones of the links 134, with the blade 40 of each blade 40/link 134 pair coupled to the drive collar 132 and the link 134 of each blade 40/link 134 pair coupled to the hub 130. For example, with respect to the first blade 40a and first link 134a identified in FIG. 2, the blade support ring 84a is inserted into the link first hole 184a. In this regard, a diameter of the hole 184a is sized in accordance with an outer diameter of the support ring 84a (e.g., slightly greater) such that while the support ring 84a will bear against a surface of the link 134a that otherwise defines the hole 184a, the support ring 84a can rotate relative to the link 134a with minimal frictional resistance akin to a journal bearing. However, the link 134a is fixed to the blade 40a in the longitudinal direction A (FIG. 6). A first connector assembly 190a (e.g., a pin and washer) captures the support ring 84a within the first hole 184a in a manner maintaining the rotatable interface.

The blade 40a is rotationally coupled to one of the coupling regions 170a of the drive collar 132. For example, the support ring 176a is inserted into the bore 80a (primarily hidden in FIG. 2). In this regard, a diameter of the bore 80a is sized in accordance with an outer diameter of the support ring 176a (e.g., slightly greater) such that while the support ring 176a will bear against a surface of the blade 40a that otherwise defines the bore 80a, the blade 40a can rotate relative to the support ring 176a (and thus relative to the drive collar 132) with minimal frictional resistance akin to a journal bearing. However, the blade 40a is fixed to the drive collar 132 in the longitudinal direction A (FIG. 6). A second connector assembly 190b (e.g., a pin and washer) captures the support ring 176a within the bore 80a in a manner maintaining the rotatable interface.

Finally, the link 134a is rotationally coupled to the one of the coupling zones 150 of the hub 130. For example, the support ring 154a is inserted into the second link hole 186a, establishing a journal bearing-type relationship. The link 134a is fixed to the hub 130 in the longitudinal direction, but can rotate relative to the hub 130 with minimal frictional interference. A third connector assembly 190c (e.g., pin and washer) captures the support ring 154a within the second link hole 186a in a manner maintaining the rotatable interface.

Figure 7:
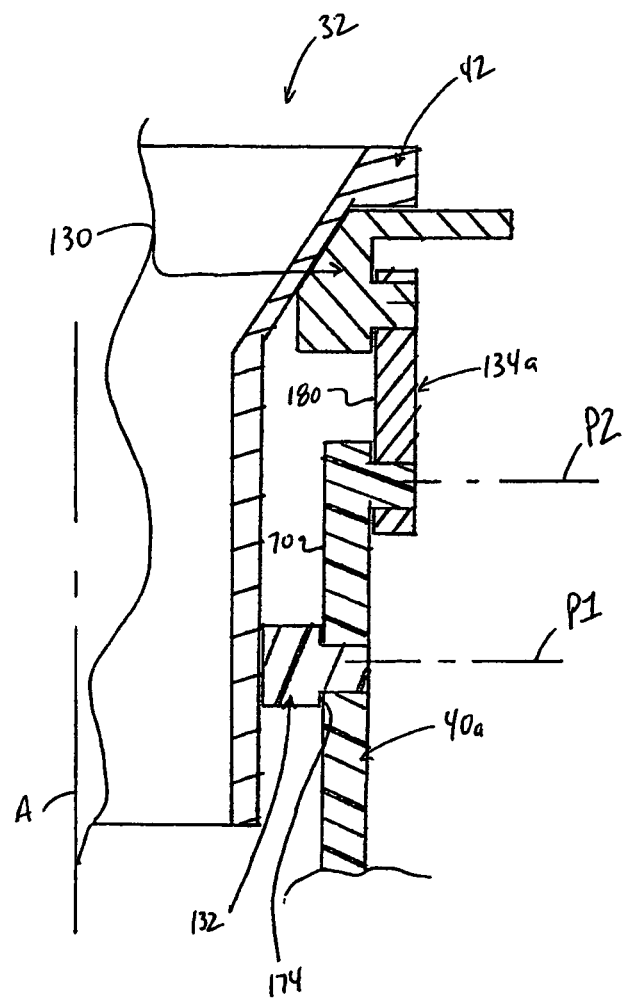
FIG. 7 is a simplified cross-sectional view of a portion of the port access device of FIG. 6.

FIG. 7 is simplified representation of the first blade 40a/link 134a pair assembled to the hub 130 and the drive collar 132. Coupling between the drive collar 132 and the blade 40a establishes a first pivot point P1 along a length of the blade 40a and about which the blade 40a can rotate; coupling between the link 134a and the blade 40a establishes a second pivot point P2 along a length of the blade 40a and about which the blade 40a can rotate. Further, the link 134a is rotatably coupled to the hub 130. With the above construction, the blade 40a is longitudinally constrained (i.e., in a direction of the central axis A) by the drive collar 132 and the hub 130 (via the link 134a). So long as the first and second pivot points P1, P2 are held stationary, the blade 40a is effectively locked relative to the port member 42 at the so-established spatial orientation. However, the rotatable couplings permit the blade 40a to pivot or rotate about the first and second pivot points P1, P2, with the substantially flat configuration allowing the bade first engagement face 70 to slide along the drive collar base 174, and the blade second engagement face 72 to slide along the link major face 180.

Figure 8B:
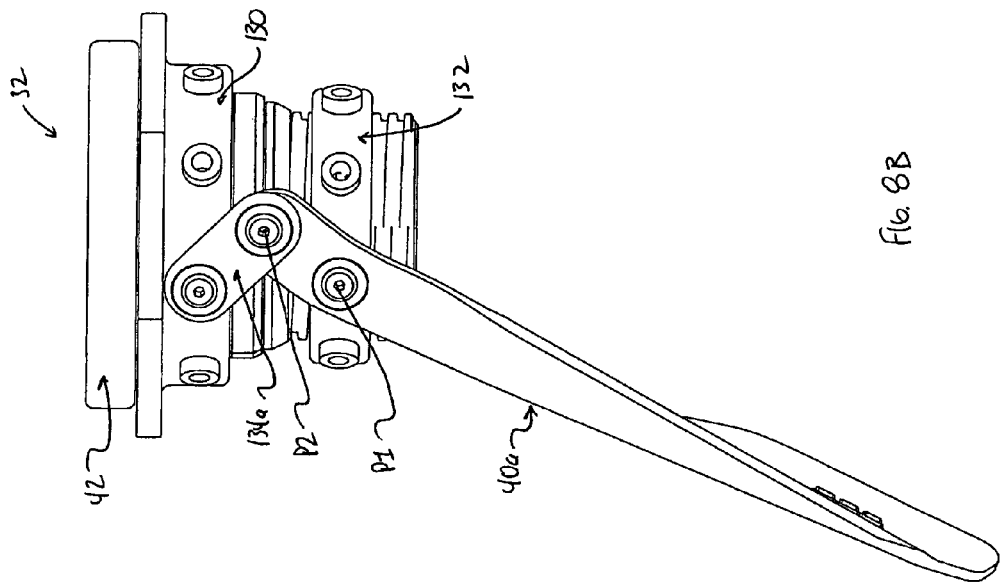
FIG. 8B is a side view of the portion of FIG. 8A and illustrating the blade in an expanded state.
Figure 8A:
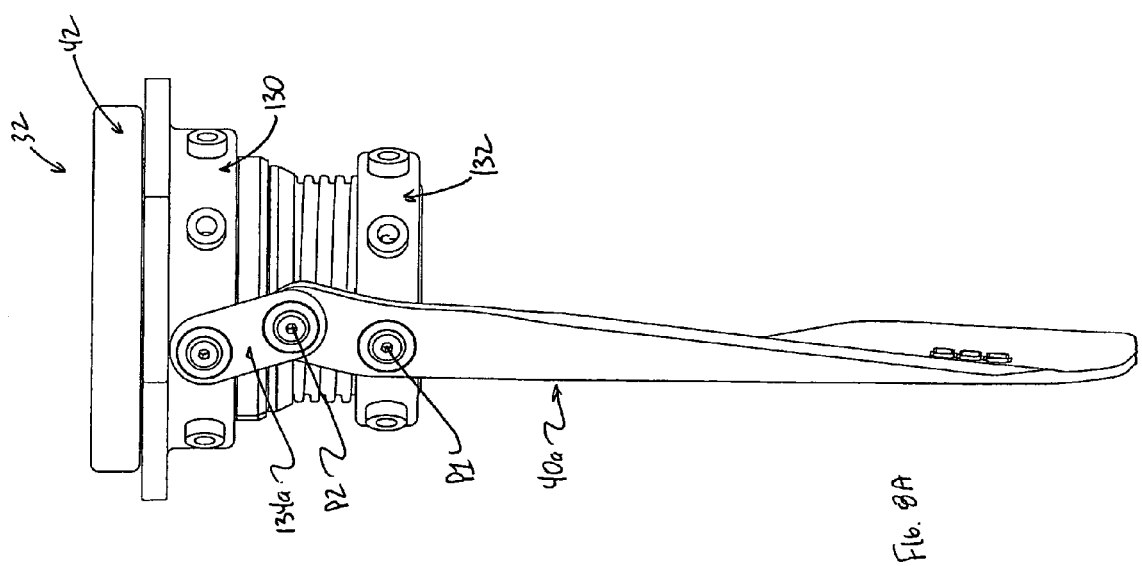
FIG. 8A is a side view of a portion of the port access device of FIG. 2, including a single one of the blades and arranged in a contracted state.

The articulation mechanism 44 as described above is configured to effectuate rotational movement by the blade 40a with rotation of the port member 42. Due to the threaded engagement, rotation of the port member 42 (about the central axis A) is translated into longitudinal movement (i.e., in a direction of the central axis A) of the drive collar 132. Longitudinal movement of the drive collar 132 generates an input force (in the longitudinal direction A) onto the blade 40a at the first pivot point P1. In response to the longitudinal input force, the blade 40a experiences spatial rotation (e.g., in a plane perpendicular to a plane of the page of FIG. 7), with the pivot points P1, P2 moving in the longitudinal direction in guiding movement of the blade 40a. For example, FIG. 8A illustrates the blade 40a in the contracted state and FIG. 8B in the expanded state. Transitioning from the contracted state to the expanded stated includes the drive collar 132 being caused to move longitudinally in a direction of the central axis A with rotation of the port member 42 (i.e., the drive collar 132 has moved longitudinally upward from the contracted state of FIG. 8A to the expanded state of FIG. 8B). The first pivot point P1 established at the coupling between the drive collar 132 and the first blade 40a is caused to move longitudinally in response to this input force, with the rotational couplings established at the first and second pivot point P1, P2 permitting the blade 40a to rotate. As shown by a comparison between FIGS. 8A and 8B, the input force has caused the first pivot point P1 and the second pivot point P2 to also move in the longitudinal direction A (i.e., upwardly in transitioning from FIG. 8A to FIG. 8B). The link 134a controls longitudinal movement of the second pivot point P2 via the rotatable coupling to the hub 130 that otherwise remains stationary relative to the port member 42 and the drive collar 132 (with rotation of the port member 42 and longitudinal movement of the drive collar 132). Rotation of the port member 42 in an opposite direction causes the blade 40a to transition from the expanded state (FIG. 8B) to the contracted state (FIG. 8A) in similar manner (with the drive collar 132 moving longitudinally, but in an opposite direction).

Figure 9A:
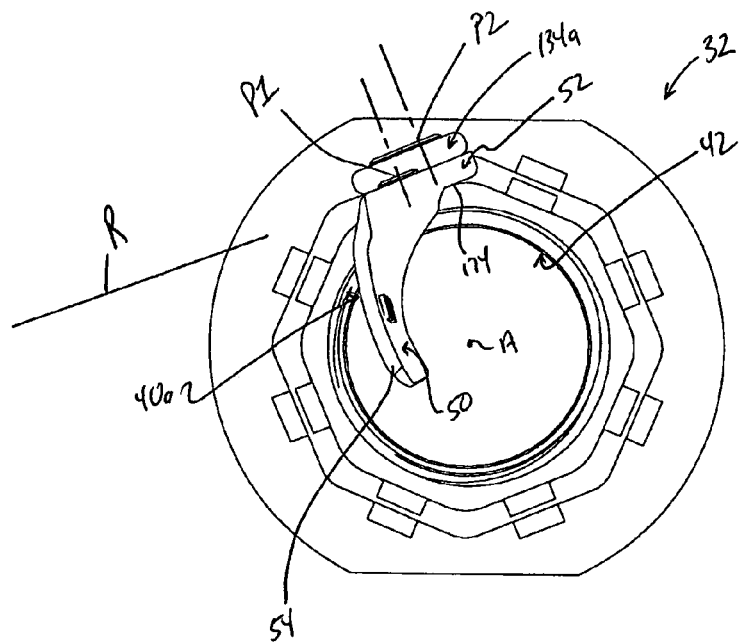
FIG. 9A is an end view of the portion of FIG. 8A.
Figure 9B:
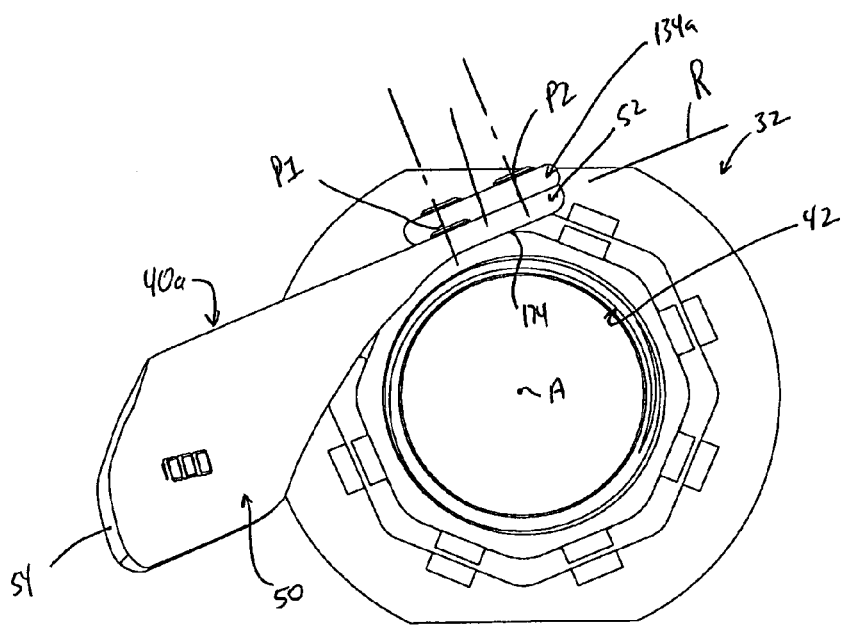
FIG. 9B is an end view of the portion of FIG. 8B.

Spatial movement of the blade 40a between the contracted and expanded states is further illustrated by a comparison of the bottom views of FIGS. 9A (contracted state) and 9B (expanded state). As a point of reference, the axis of rotation established by each of the pivot points P1, P2 extends through the port member 42; in other words, the pivot point axes P1, P2 are non-tangential relative to a circumference of the port member 42. However, the shaft 52/drive collar base 174 establishes a substantially planar interface in which the shaft 52 rotates. Stated otherwise, the shaft 52 rotates in a plane R that is substantially tangent (e.g., within 10% of a truly tangential relationship) to a circumference of the port member 42. Due to the substantially perpendicular arrangement of the blade body 50 relative to the shaft 52 (and thus relative to the plane R), although a radial location of the shaft 52 relative to the central axis A does not change in transitioning between the contracted and expanded states, the blade body 50 exhibits an apparent radial movement relative to the central axis A. The tip 54 is closely proximate the central axis A in the contracted state, and is radially spaced a significant distance from the central axis A in the expanded state.

Returning to FIG. 2, each of the blades 40/links 134 are coupled to the hub 130 and the drive collar 132 as described above, and are circumferentially aligned about the port member 42. As shown in FIG. 6, with this arrangement, the blades 40 extend distally from the port member 42 and collectively define an access region 200 that is open to, and aligned with, the central passageway 100. Thus, a surgical instrument (not shown) inserted through the central passageway 100 passes between the blades 40 via the access region 200 and can be manipulated distally beyond the tips 54. With the circumferential arrangement of the blades 40, adjacent ones of the blades 40 overlap one another in at least the collapsed state as shown in FIG. 10A. Further, the tips 54 collectively define a collapsed diameter D1. For reasons made clear below, the collapsed diameter D1 is less than an outer dimension of the flange 160. In the expanded arrangement of FIG. 10B, the tips 54 collectively define an expanded diameter D2 that is greater than the collapsed diameter D1. A comparison of FIGS. 10A and 10B further illustrates the collective motion of the blades 40 in transitioning between the collapsed and expanded states, akin to a blooming flower. To assist in better understanding motion of the blades 40, the first blade 40a is identified in each of FIGS. 10A and 10B. As shown, the blades 40 rotate in a plane that is tangent to a circumference of the port member 42 (or in a plane that is parallel to a plane tangent to the port member 42). Thus, the blades 40 do not move solely in the radial direction relative to the central axis A. However, a significant change in the effective diameter collectively defined by the tips 54 is achieved, with the blade body 54 of each of the blades 40 being shaped such that in the expanded state, the access region 200 (referenced generally) has an increasing diameter in distal extension from a location adjacent the port member 42 to the tips 54 (e.g., expanding from the collapsed diameter D1 of about 75 mm to the expanded diameter D2 of about 180 mm in some non-limiting embodiments).

A comparison of FIGS. 10C (contracted state) and 10D (expanded state) illustrates that the first pivot points Pb collectively move in longitudinal direction in transitioning between the contracted and expanded states, as do the second pivot points P2. Further, the tips 54 remain co-planar each state in some embodiments.

Optional Articulation Feedback and Control

In some embodiments, surgical access systems of the present disclosure are configured to provide a user with feedback information indicative of the extent to which the blades 40 have been expanded (and a size of a surgical field established by the expanded blades). For example, FIG. 11A illustrates an expansion indicator 202 (referenced generally) optionally provided with the port access device 32. The indicator 202 includes a measurement scale 204 and a reference marker 206. The measurement scale 204 is applied (inscribed, printed, labeled, etc.) to a surface of the hub 130, such as along an upper surface of the flange 160. The measurement scale 204 can assume various formats implicating incremental distances (e.g., the spaced hash marks as shown), and can include one or more numerical indicia, etc. The reference marker 206 is attached to the port member 42, arranged to visually align with the indicia of the measurement scale 204. The reference marker 206 can be shaped as a triangle, arrow, etc. Regardless, because the reference marker 206 is affixed to the port member 42 and because the port member 42 can rotate relative to the hub 130, an arrangement of the reference marker 206 relative to the measurement scale 204 changes with rotation of the port member 42, and thus with expansion/contraction of the blades 40. Thus, a visual relationship of the reference member 206 relative to the measurement scale 204 is indicative on an extent of expansion of the blades 40 and of a size of the surgical field established by the blades 40.

More particularly, the blades 40 are arranged in the collapsed state in FIG. 11A, with the reference marker 206 at a first arrangement relative to the measurement scale 204. As the port member 42 is rotated (in the direction indicated by the arrow 208) and the blades 40 expand, the reference marker 206 moves relative to the measurement scale, for example to the arrangements of FIGS. 11B (partially expanded state) and 11C (fully expanded state), with each sequentially different arrangement providing the user with a visual indication of the extent of blade expansion, and thus a size of the surgical field established by the blades 40.

While the expansion indicator 202 has been shown and described as being mechanical in nature, other formats are also acceptable. For example, an electrically-based measurement device can be employed (e.g., rotary encoder, potentiometer, etc.). In related embodiments, surgical access systems of the present disclosure can be configured to provide a user with extent of blade expansion information in other forms, such as audible "beeps", colored lights, etc. Even further, systems of the present disclosure can be configured to provide the user with an alert or warning (audible, visual or both) when the blades 40 are approaching or have exceeded a maximum extent of expansion. For example, a particular patient or procedure may dictate that the surgical field established by the blades 40 not exceed a certain size, and the port access device 32 is capable of providing an expanded state in which the blades 40 expand beyond this desired maximum size. Under these conditions, a logic device/controller (not shown) associated with the port access device 32 can be programmed to monitor the measured extent of blade expansion as described above, and generate a warning (audible, visual or both) when the measured blade expansion is nearing or at the maximum desired surgical field size.

In addition to, as an alternative to, the expansion indicators described above, surgical access systems of the present disclosure can optionally be configured to provide feedback information relating to the torque being applied to the port member 42. As a point of reference, with many surgical procedures, the blades 40 contact and press against tissue, organs, etc., when transitioning toward the expanded state. The contacted tissue, organs, etc., thus resist expansion of the blades 40, in turn requiring an increase in the torque applied to the port member 42 in order to effectuate further expansion. At or above certain force levels, however, the contacted tissue, organs, etc., may experience undesired trauma. Thus, users may benefit from understanding the force being applied to the tissue, organs, etc.

Figure 12A:
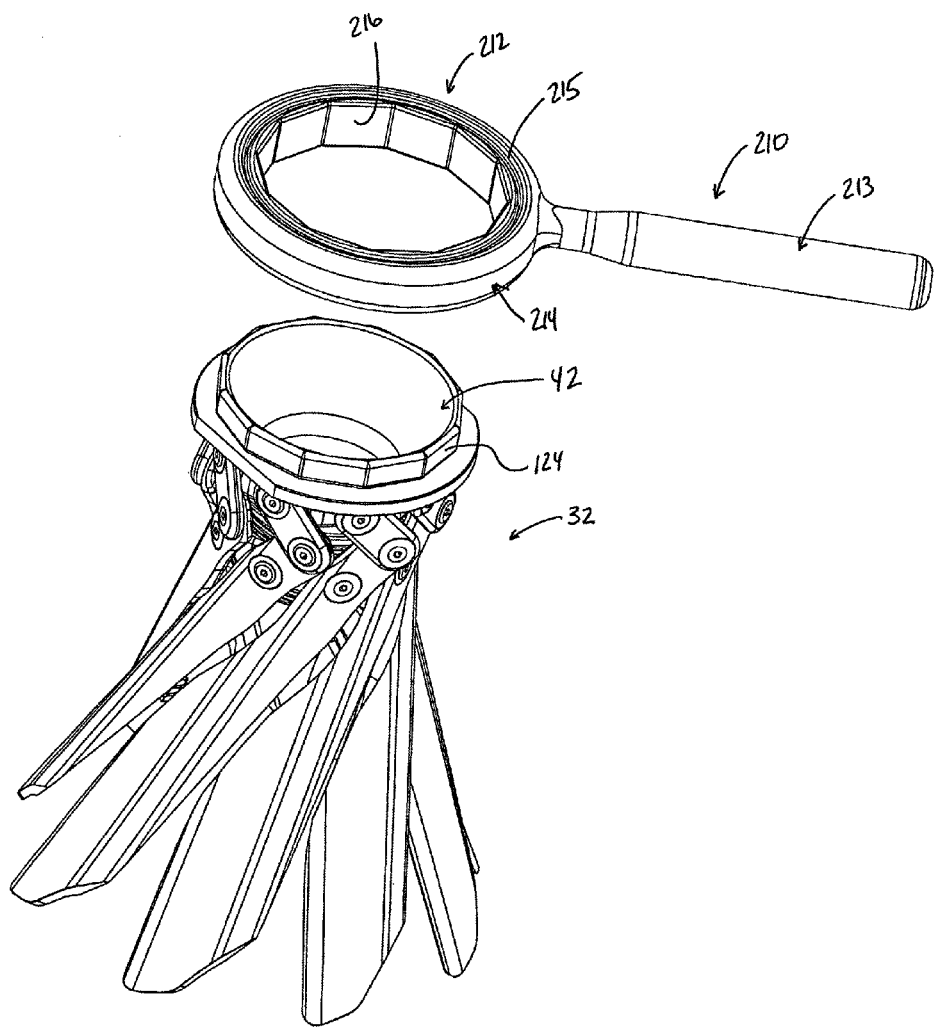
FIG. 12A is a perspective view of another surgical access system in accordance with principles of the present disclosure.

With the above in mind, a torque device 210 useful with surgical access systems of the present disclosure is shown in FIG. 12A. The torque device 210 includes a head assembly 212 and a handle 213. The head assembly 212 includes a frame 214 coupled to (or formed integrally with) the handle 213 and carrying at least one torque sensor 215 (referenced generally). The frame 214 further defines an engagement surface 216 configured to selectively couple with the gripping surface 124 of the port member 42. The torque sensor 215 can assume various forms known in the art (e.g., magnetic torque sensor, electrical-based torque transducer, etc.). Torque (applied by the torque device 210 on to the port member 42) as measured by the torque sensor 215 can be displayed to a user by a display (not shown) carried by the head assembly 212 or the handle 213. In other embodiments, the torque device 210 can be configured to signal (wired or wireless) measured torque to a separate display device.

Figure 12B:
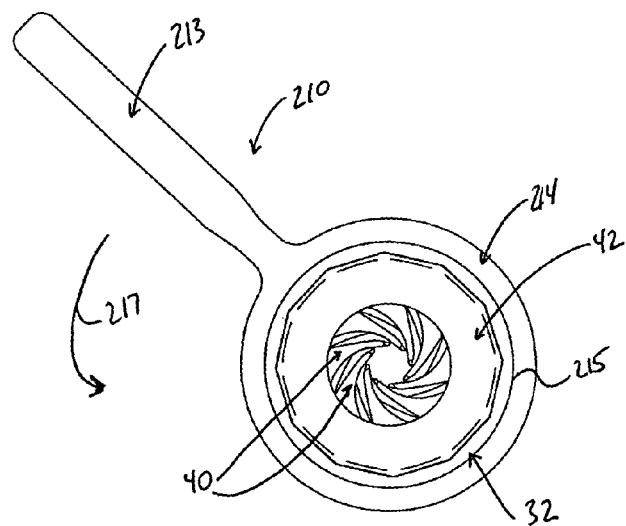
FIGS. 12B and 12C are top views illustrating use of the system of FIG. 12A.
Figure 12C:
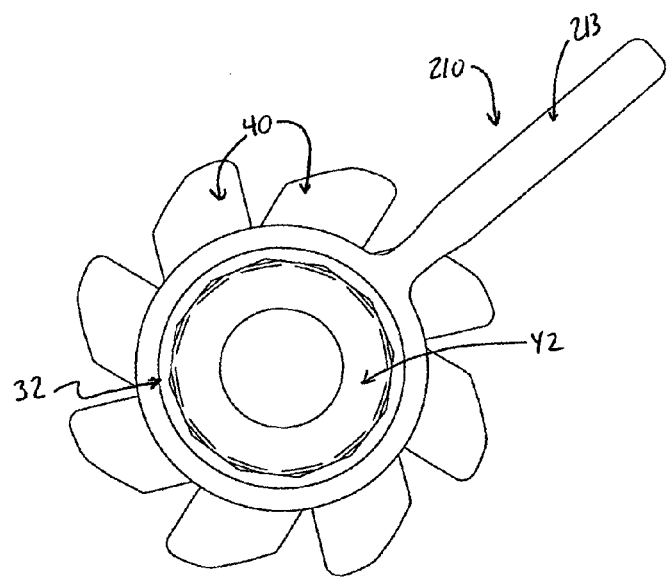

During use, the frame 214 is coupled to the port member 42 as shown in FIG. 12B. The port access device 32 can be transitioned from the collapsed state of FIG. 12B toward the expanded state of FIG. 12C by a user grasping and applying a torque onto the handle 213 (e.g., moment force in a direction of the arrow 217 in FIG. 12B). The so-applied force causes the port member 42 to rotate, and thus the blades 40 to expand (or collapse). The torque sensor 215 measures the force being applied to the port member 42 that in turn is indicative of the force the blades 40 are applying on to contacted tissue, organs, etc.

In some embodiments, the user monitors the measured (and displayed) torque readings, and self-evaluates whether the applied torque is indicative of the pressing force being applied to tissue, organs, etc., as at or exceeding a desired or safe level. In other embodiments, the torque device 210 (or another system component receiving torque measurement information from the torque device 210) is configured to generate an alert or warning (audible, visual or both) that the sensed torque is approaching or has exceeded a pre-determined maximum level.

While the torque sensor 215 can provide useful information to a user, in other embodiments, the torque sensor 215 can be omitted. The corresponding torque device 210 thus serves as a simple, ergonomic tool that assists a user in more easily rotating the port member 42 to effectuate movement of the blades 40.

Optional Illumination Devices

As made clear by the above explanations, the port access devices 32 of the present disclosure provide retraction and direct visualization of the surgical field. In some embodiments, additional lighting features can be provided. For example, FIG. 10B best illustrates that one or more LEDs 220 can optionally be assembled to the interior surface 60 of each of the blades 40 adjacent the corresponding tip 54. The number and type of LEDs 220 can vary, and in some embodiments, the LEDs 220 are provided on less than all of the blades 40. The LEDs 220 can be powered in various manners, for example via an external power source (not shown). Alternatively, and as illustrated in FIG. 13, a battery 230 or other power source can be assembled to each of the blades 40. In yet other embodiments, systems of the present disclosure can further include an illumination assembly 240 as shown in FIGS. 14A and 14B. The illumination assembly 240 includes a light ring device 242 and an optional transmission body 244. The light ring device 242 carries one or more lights (hidden), for example LEDs, within a shroud 246. A cable 248 provides power to the lights. The transmission body 244 is assembled to the port access device 32, and can assume various forms configured to direct light from the light ring device 242 to an interior of the port access device 32 (and within the blades 40). For example, the transmission body 244 can be a tube, such as a translucent glass tube, a translucent plastic tube, etc., mounted to the port member 42. The transmission body 244 is sized to selectively receive the shroud 246, with the shroud 246 and transmission body 244 having an opening 250 (referenced generally) through which surgical instruments can be introduced. When the shroud 246 is mounted to the transmission body 244, light waves emitted by the lights of the light ring device 242 are directed by the transmission body 244 to locations within the blades 40 thus illuminating the surgical field. Moreover, an interior of the transmission body 244 is illuminated, providing the surgeon with a clear, direct view of the surgical field. Thus, the surgeon is not required to rely on lighting from light source outside of the patient as is conventionally employed. In fact, in other embodiments, the port access devices and systems of the present disclosure can consist solely of a translucent glass or plastic tube and a light source. The translucent tube is inserted through the incision and the light source directly connected to the tube outside of the patient. The translucent tube transilluminates itself and the surgical field, and serves as a port through which surgical instruments can be inserted. With yet other embodiments of surgical access systems of the present disclosure, auxiliary illumination is omitted.

Alternative Blade Constructions

Figure 15A:
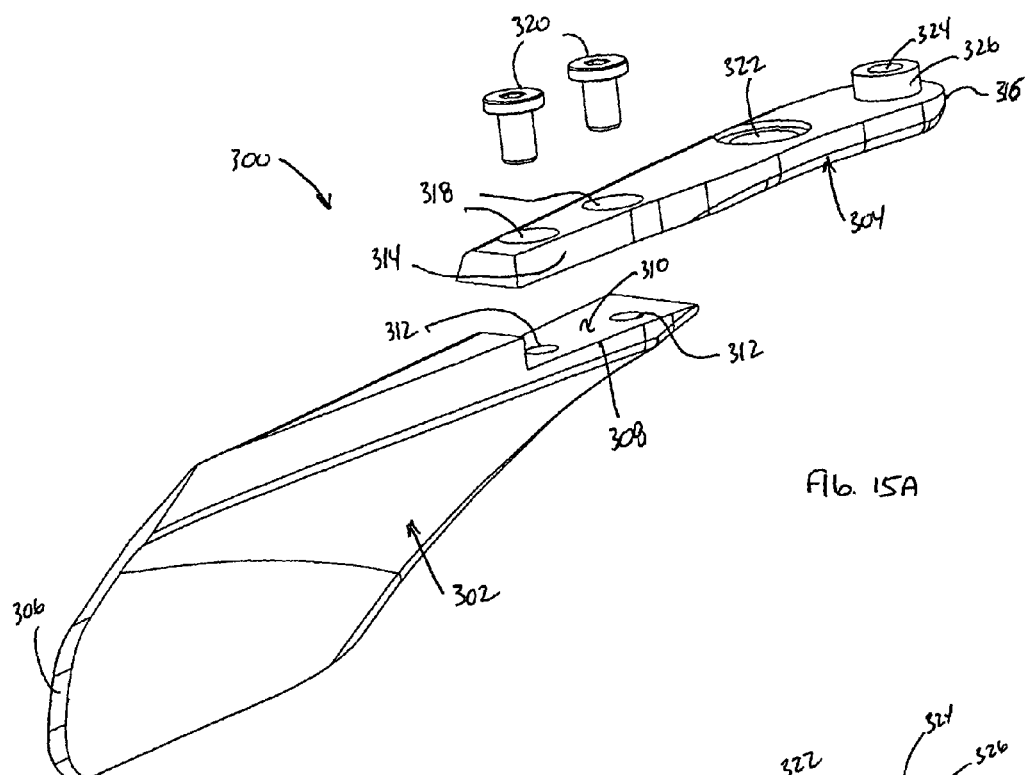
FIG. 15A is an exploded perspective view of an alternative blade useful with the port access device of FIG. 2.

While the port access device 32 has been illustrated as providing each of the blades 40 as an integral, homogenous body, in other embodiments, the blades can consist of two (or more) components. For example, FIG. 15A illustrates an alternative blade 300 useful with surgical access systems of the present disclosure. The blade 300 includes a blade body 302 and a shaft 304. In many respects, the blade 300 is highly akin to the blade 40 (FIG. 3A) described above, but with the construction of FIG. 15A, the blade body 302 and the shaft 304 are separately formed and subsequently assembled (and later disassembled) from one another by a user. Thus, the blade body 302 can have the shape and size attributes described above with respect to the blade body 50 (FIG. 3A), and extends between a tip 306 and a mounting region 308. The mounting region 308 is configured for selective assembly with the shaft 304, and in some embodiments forms an engagement face 310 and one or more apertures 312. The engagement face 310 can be substantially flat (e.g., within 10% of a truly flat surface) for flush abutment with the shaft 304.

The shaft 304 can have the shape and size attributes described above with respect to the shaft 52 (FIG. 3A), and extends between a blade region 314 and a coupling end 316. The blade region 314 is configured for selective attachment to the blade body 302. For example, one or more holes 318 can be provided and facilitate assembly with the aperture(s) 312 in the blade body 302 via a fastener(s) 320 (e.g., a screw). To better ensure robust engagement, a surface (hidden) of the blade region 314 otherwise "facing" the engagement face 310 can be substantially flat. Regardless, first and second bores 322, 324 are formed through a thickness of the shaft 304 adjacent the coupling end 316, and are akin to the bores 80, 82 (FIG. 3A) described above. In some embodiments, the second bore 324 (and/or the first bore 322) can be defined or surrounded by a support ring 326 as previously described. The first bore 322 provides for rotatable coupling to the drive collar 132 (FIG. 2) and the second bore 324 provides for rotatable coupling to one of the links 134 (FIG. 2). Thus, a distance between the first and second bores 322, 324, as well as a location of the second bore 324 relative to the coupling end 316 of the shaft 304, is pre-determined in accordance with other geometric attributes of the port access device 32/articulation mechanism 44 (FIG. 2). In other words, the fully assembled blade 300 will interface with articulation mechanism 44 as described above.

Figure 15B:
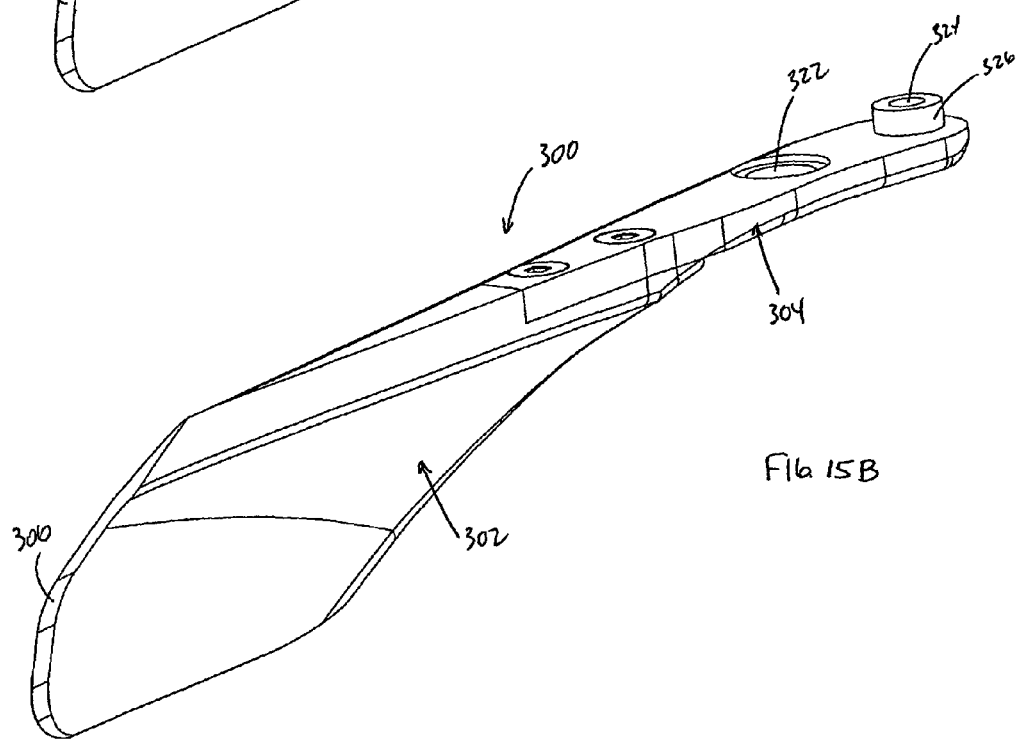
FIG. 15B is a perspective view of the blade of FIG. 15A upon final assembly.

While the blade body mounting region 308 has a pre-determined configuration in accordance with the blade region 316 of the shaft 302, a remainder of the blade body 302 can have a multitude of differing shapes and/or sizes. With this configuration, then, a user can select a desired blade body shape or length best suited for a particular procedure, and mount the so-selected blade body 302 to the shaft 302. Once assembled (as in FIG. 15B), the blade 300 is utilized with the port access device 32 as described above. To perform a different procedure having differing anatomical constraints (e.g., the surgical field is at a different depth relative to the patient's skin), the blade body 302 can be replaced with a differently sized and/or shaped component.

Figure 16A:
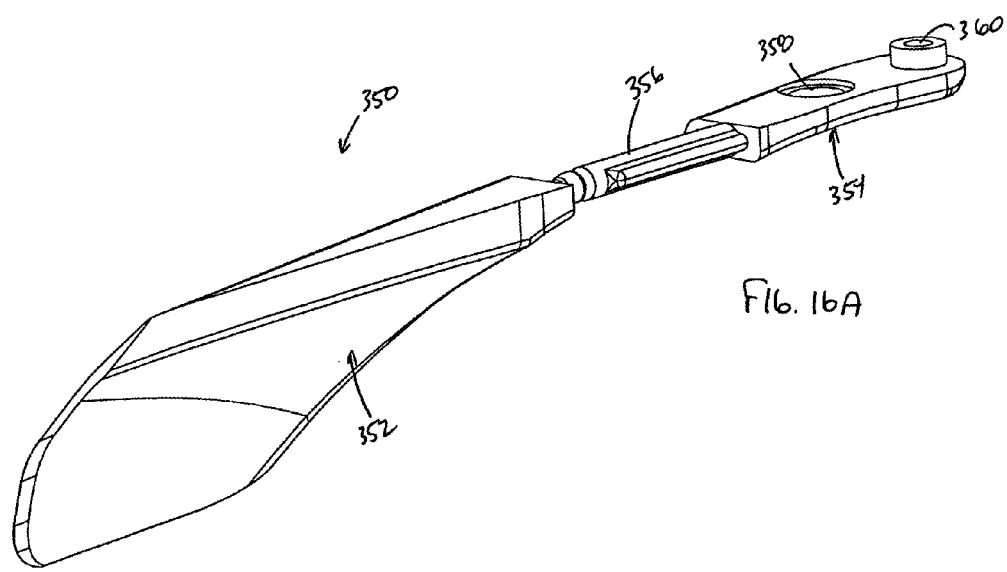
FIG. 16A is an exploded perspective view of another alternative blade useful with the port access device of FIG. 2.
Figure 16B:
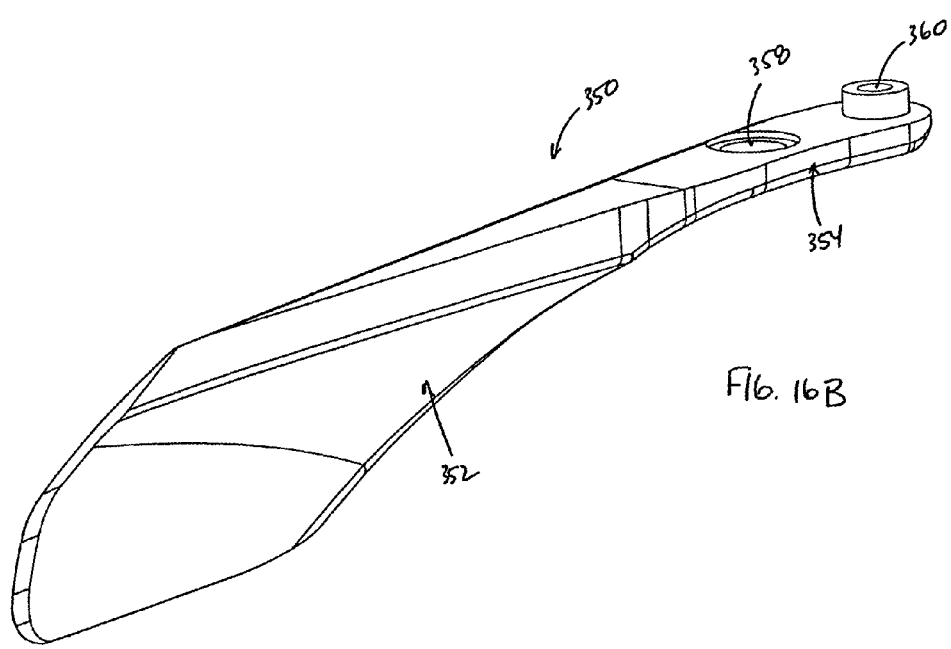
FIG. 16B is a perspective view of the blade of FIG. 16A upon final assembly.

The screw-type connection associated with the interchangeable blade 300 is but one acceptable approach envisioned by the present disclosure. FIGS. 16A and 16B illustrate another embodiment blade 350 useful with surgical access systems of the present disclosure, and includes a blade body 352 and a shaft 354. The blade body 352 is selectively assembled to the shaft 354 via a snap on-type construction. For example, the shaft 354 can form a shank 356 configured to be mounted within a channel (hidden) formed by the blade body 352 in a snap-fit relationship. The shaft 354 forms the first and second bores 358, 360 as described above.

Anchoring Device 34

Returning to FIGS. 1A and 1B, the surgical access systems 30 of the present disclosure optionally include the anchoring device 34. The anchoring device 34 can assume a variety of forms, and in generally configured to support the port access device 32 relative to the patient and the incision through which the port access device 32 is inserted. In some embodiments, the anchoring device 34 is configured to facilitate controlled, spatial rotation of the port access device 32 relative to the patient, and to "lock" the port access device 32 relative to the patient once a desired orientation has been obtained.

Figure 17A:
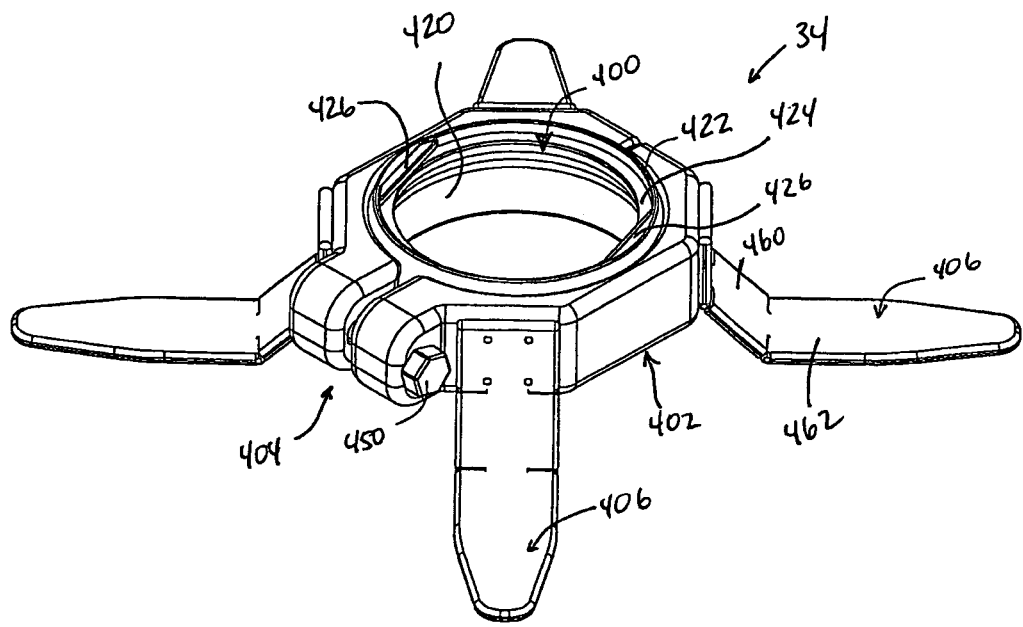
FIGS. 17A-17D are perspective views of an anchoring device useful with the system of FIG. 1A.

One embodiment of the anchoring device 34 is shown in greater detail in FIG. 17A, and includes a receiving body 400, an outer frame 402, a locking mechanism 404 and a plurality of platforms 406. In general terms, the receiving body 400 and the outer frame 402 combine to define a receiving apparatus providing ball joint arrangement for rotatably supporting the port access device 32 (FIG. 1A). The locking mechanism 404 is operable to selectively lock the receiving body 400 relative to the outer frame 402. Finally, the platforms 406 project from the outer frame 402 and provide surfaces for temporarily securing the anchoring device 34 relative to the patient (not shown) and/or to another article secured to the patient.

The receiving body 400 is configured to nest within the outer frame 402, and defines a central aperture sized 420 and shaped in accordance with the port access device 32 (FIG. 1A). More particularly, the central aperture 420 is sized to permit passage there through of the blades 40 (FIG. 1A) in at least the contracted stated. Further, the receiving body 400 includes one or more features designed in accordance with complimentary features of the port access device 32 to permit selective mounting of the port access device 32 to the receiving body 400. For example, the receiving body 400 terminates at a leading edge 422. A circumferential shelf 424 is formed adjacent to, but longitudinally spaced from, the leading edge 422. Finally, opposing lips 426 are each formed as a radially-inward extension from the leading edge 422, and are longitudinally spaced from the shelf 424.

A diameter of the aperture 420 at the leading edge 422 (apart from the lips 426) is greater than a diameter of the shelf 424. A lateral distance between the lips 426 is less than a diameter of a remainder of the leading edge 422, and can approximate the diameter of the shelf 424. The diameter of the leading edge 422, the distance between the lips 426, and the diameter of the shelf 424 corresponds with an outer dimension of the port access device flange 160 (FIG. 5A). More particularly, the receiving body 400 and the flange 160 have complimentary constructions such that the flange 160 can be inserted between lips 426 (i.e., the flat side edges 162, 164 (FIG. 5A) are aligned with the lips 426) and into abutment with the shelf 424. With subsequent rotation of the flange 160 relative to the receiving body 400, a thickness of the flange 160 is captured between the lips 426 and the shelf 424, thereby affixing the flange 160 (and thus the port access device 32) to the receiving body 400 (and thus the anchoring device 34). The port access device 32 can be released from the anchoring device 34 in a reverse fashion. The receiving body 400 can alternatively incorporate a wide variety of other features that effectuate releasable coupling with the port access device 32 that may or may not implicate the shelf 424 and lips 426 as shown.

Figure 17B:
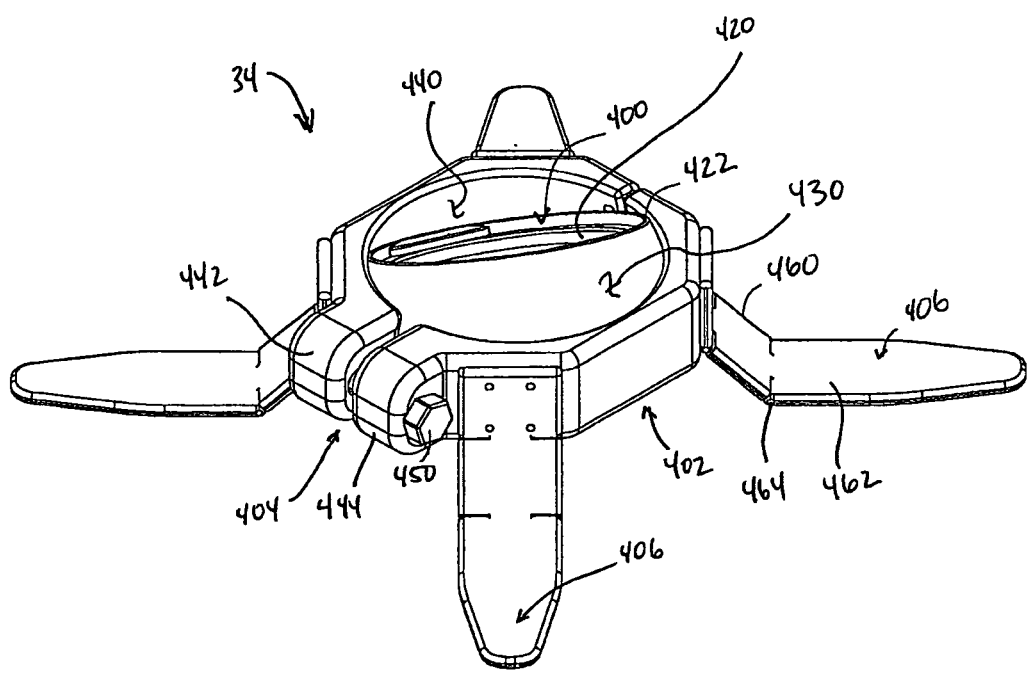

Regardless of the features by which the receiving body 400 couples to or otherwise holds the port access device 42 (FIG. 1A), an outer surface 430 of the receiving body 400 forms a semi-spherical shape as best shown in FIG. 17B. Because the central aperture 420 extends through an entirety of the receiving body 400, the outer surface 430 is not a complete sphere. However, the semi-spherical shape of the outer surface 430 facilitates rotatable coupling with the outer frame 402.

The outer frame 402 can assume various forms for maintain the receiving body 400 and generally defines an interior socket surface 440 (best seen in FIG. 17B). The socket surface 440 is configured to rotatably capture the semi-spherical outer surface 430 of the receiving body 400. In this regard, the socket surface 440 generally defines a diameter sized to permit a wide range of rotational movement of the receiving body 400 relative to the outer frame 402 as reflected by a comparison of FIGS. 17B and 17C. In some embodiment, the outer frame 402 is band-like body, terminating at opposing ends 442, 444. The opposing ends 442, 444 are separated from one another or not otherwise homogenously formed. With this construction, the diameter of the socket surface 440 can be slightly altered by moving the opposing ends 442, 444 toward or away from one another.

The locking mechanism 404 can be described as including the opposing ends 442, 444 of the outer frame 402, as well as a fastener 450 (e.g., a screw). The fastener 450 interconnects the ends 442, 444. Manipulation of the fastener 450 forces the opposing ends 442, 444 toward one another to reduce a diameter of the socket surface 440, frictionally capturing or preventing movement of the receiving body 400. Conversely, as the fastener 450 is loosened, the diameter is slightly increased/frictional interface with the receiving body 400 is lessened to permit the receiving body 400 to rotate relative to the outer frame 402. With this construction, then, a user can spatially position the receiving body 400 relative to the outer frame 402 as desired, and then operate the locking mechanism 404 to "lock" the receiving body 400 in the selected orientation. The locking mechanism 404 can assume a wide variety of other forms capable of providing this optional feature. In other embodiments, the locking mechanism 404 can be omitted.

Figure 17C:
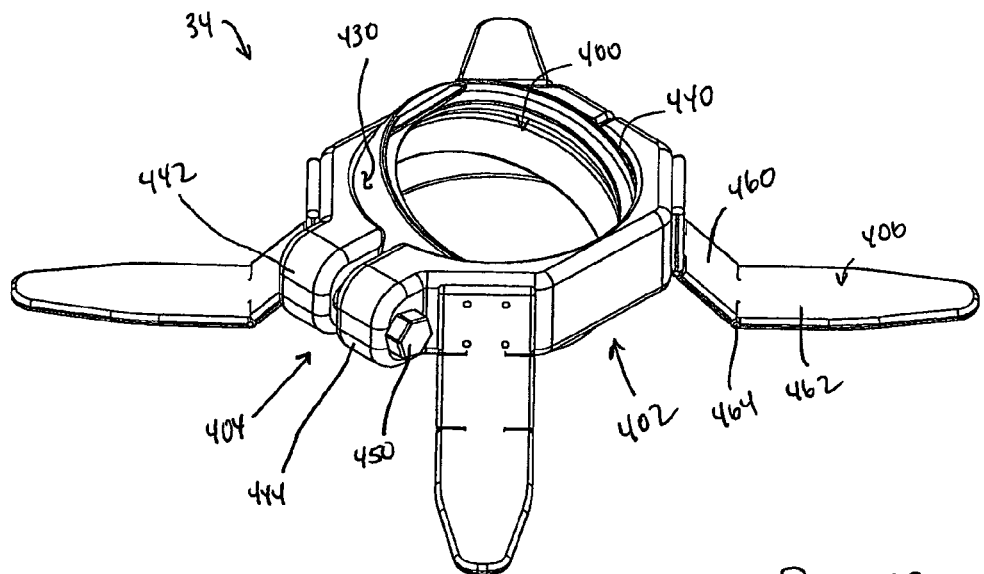
Figure 17D:
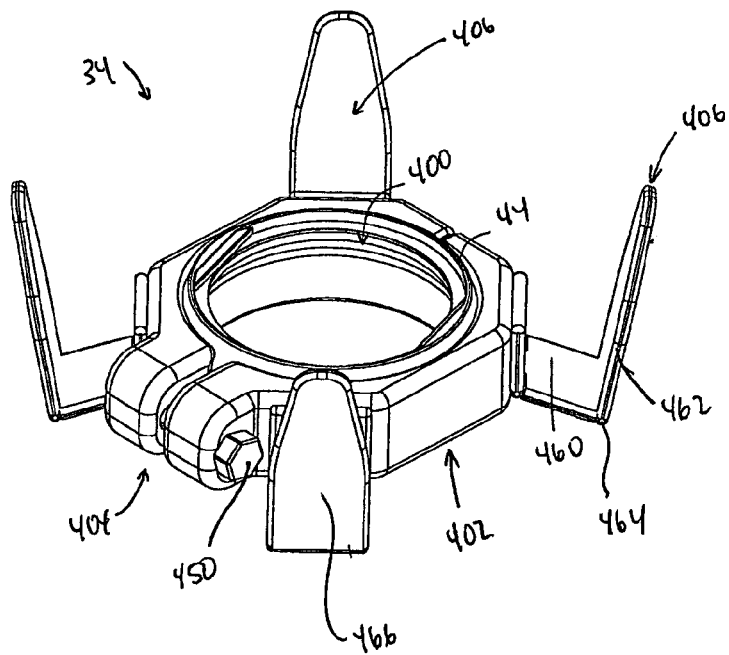

The platforms 406 extend from the outer frame 402, and in some embodiments are identical. While FIGS. 17A-17C illustrate the anchoring device 34 has having four of the platforms 406, any other number, either greater or lesser, is also acceptable. In some embodiments, one or more or all of the platforms 406 define a first section 460 and a second section 462. The first section 460 is attached to and projects generally radially and longitudinally downwardly from the outer frame 402. The second section 462 extends from the first section 460, and in some embodiments is connected to the first section 460 by a hinge 464 (e.g., the hinge 464 can be a living hinge formed into the platform 460). As best shown in FIG. 17D, the hinge 464 facilitates arrangement of the second section 462 as desired by a user. FIG. 17D further illustrates a bottom surface 466 of the platform 406. The bottom surface 466 optionally forms or carries a component conducive to attachment to other materials commonly employed in surgical suites. For example, a hook-and-loop material (e.g., Velcro®) can be applied to the bottom surface 466 for securement to a surgical drape or similar article. In other embodiments, the platforms 406 can assume a number of other forms that may or may not include the hinge 464 and/or the formatted bottom surface 466.

Methods of Use

Figure 18A:
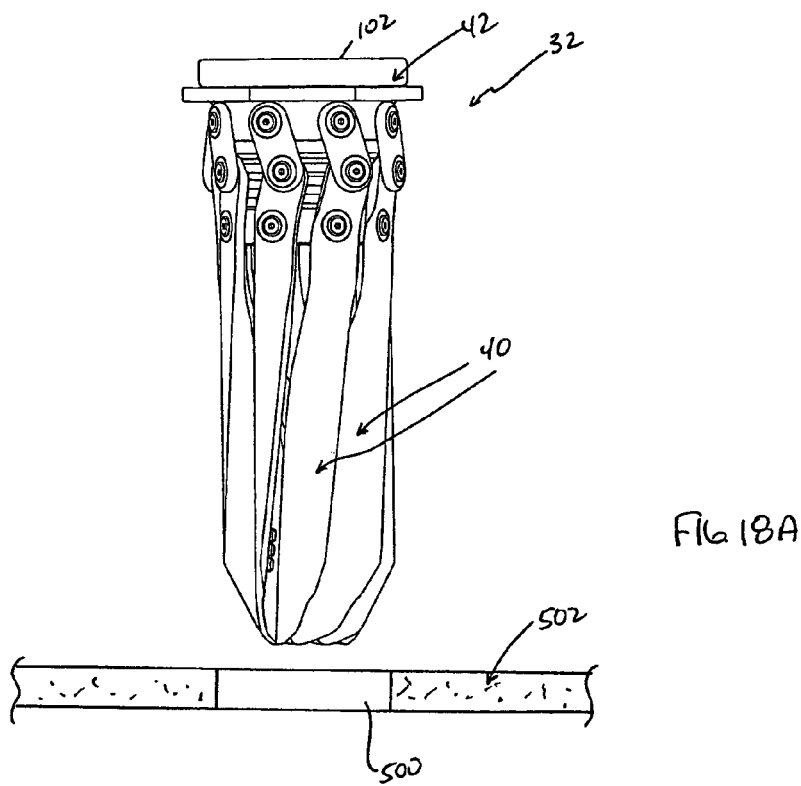
FIGS. 18A-18C illustrate use of a port access device to perform a surgical procedure in accordance with principles of the present disclosure.

Returning to FIG. 1A, the port access device 32 can be employed apart from the anchoring device 34 to perform various surgical procedures. That is to say, surgical access systems in accordance with principles of the present disclosure can consist solely of the port access device 32, and the anchoring device 34 is optional. With this in mind, as shown in FIG. 18A, the blades 40, in the contracted state, can be inserted through a relatively small incision 500 through skin 502 of a patient. Because the blades 40 collectively define a relatively small outer diameter in the contracted state, the incision 500 can be much smaller than incisions normally required for conventional open surgery procedures. For example, in some embodiments, an external diameter or dimension collectively defined by the blades 40 is on the order of 75 mm, meaning that the incision 500 need only have a length of approximately 80 mm. This feature allows the surgery to be conducted under IV sedation/local anesthesia, and without general anesthesia. Regardless, the proximal end 102 of the port member 42 remains external the patient (i.e., outside or above the skin 502) and the central passageway 100 (FIG. 6) is fully accessible to the surgeon.

Figure 18B:
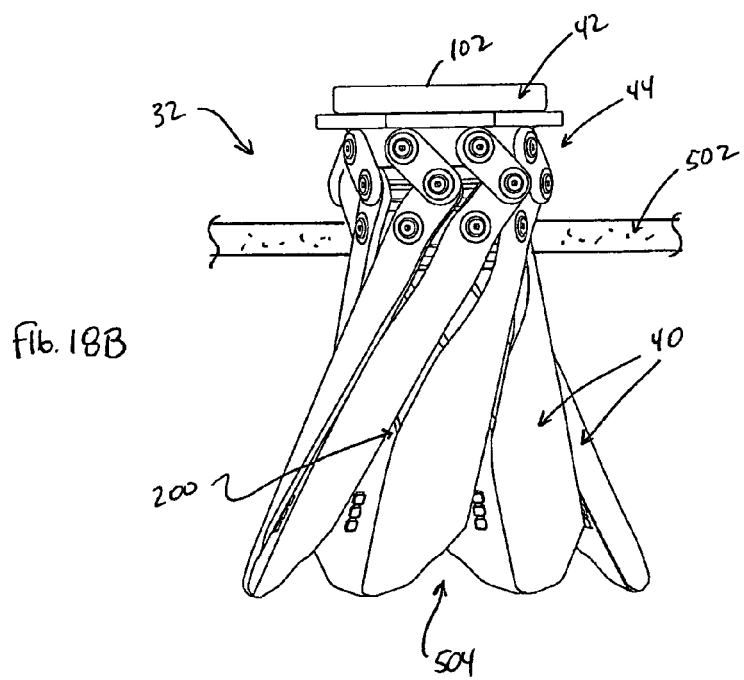
Figure 18C:
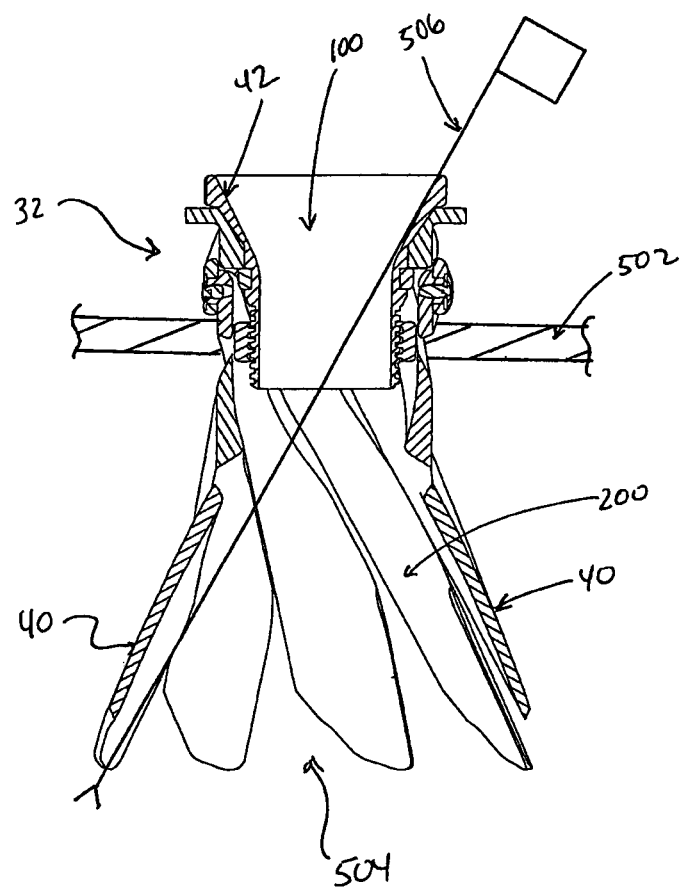

Once inserted, the articulation mechanism 44 can be operated as described above (e.g. the port member 42 rotated), causing the blades 40 to transition to or toward the expanded state as shown in FIG. 18B. With this transitioning, the blades 40 robustly press against and retract contacted bodily tissue and organs (not shown), thereby generating an enlarged surgical field 504 at the access region 200 (referenced generally in FIG. 18B). The surgeon has direct visualization of the surgical field, and auxiliary viewing instruments are not necessary. Where provided, any of the optional lighting devices described above can be activated to more fully illuminate the surgical field 504. Various surgical instruments are deployed to the surgical field 504 via the port passageway 100 and the access region 200 as shown in FIG. 18C (surgical instrument 506 is illustrated schematically in FIG. 18C). In this regard, geometries of the port member 42 and the blades 40 are such that in some embodiments, the surgical instrument 506 can be inclined up to 60 degrees.

Figure 19A:
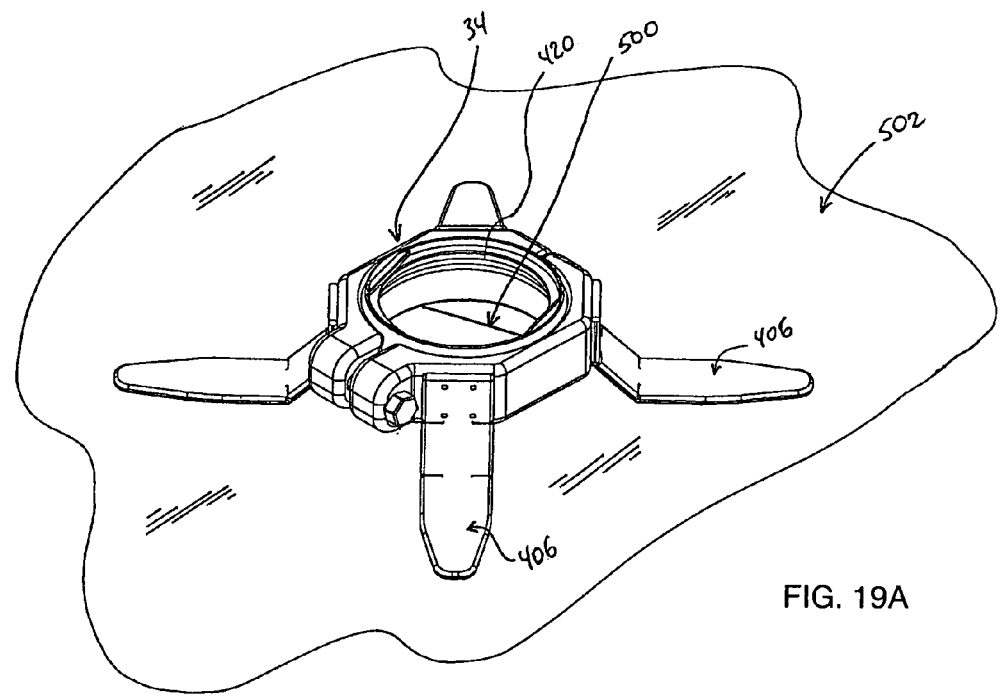
FIGS. 19A-19E illustrate use of a port access device and an anchoring device to perform a surgical procedure in accordance with principles of the present disclosure.
Figure 19C:
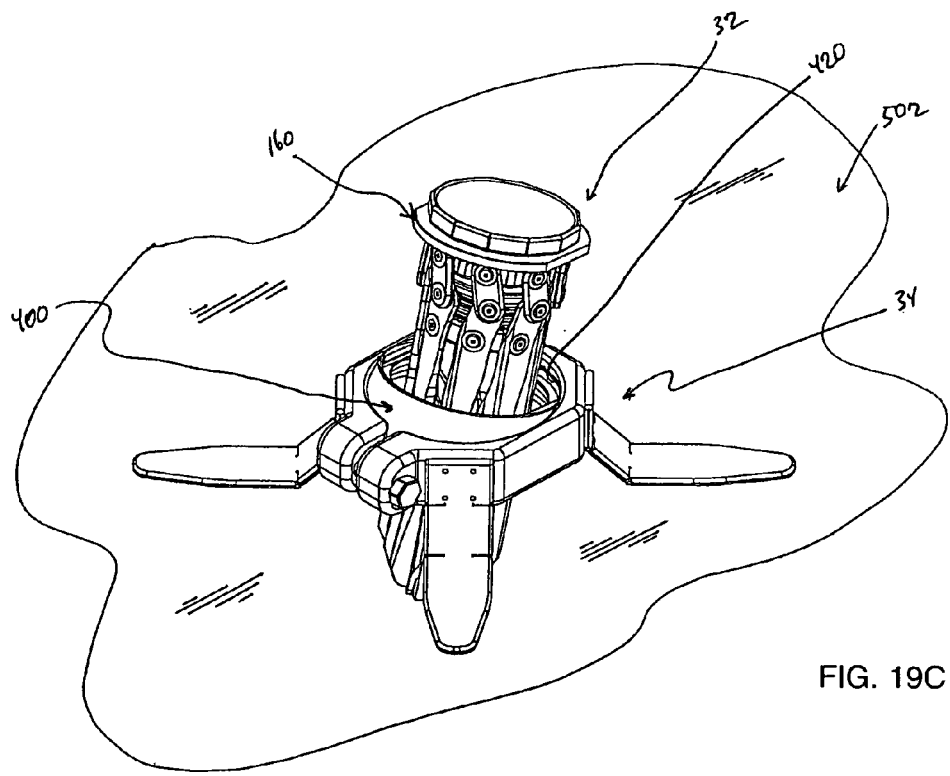
Figure 19B:
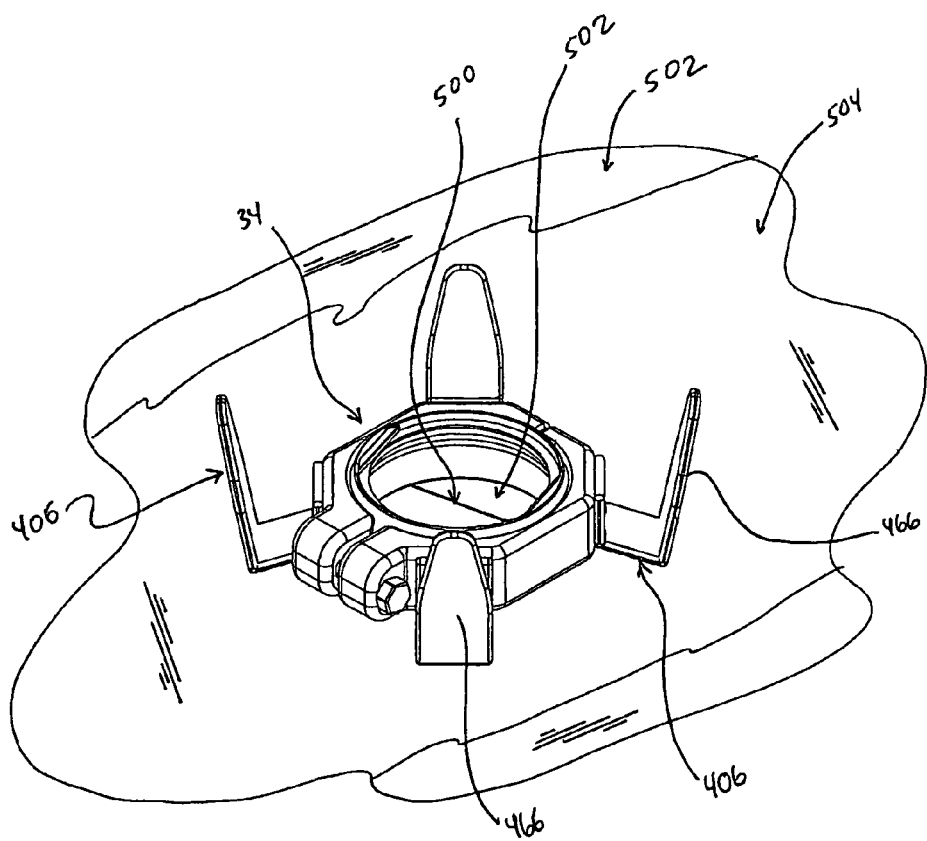
Figure 19D:
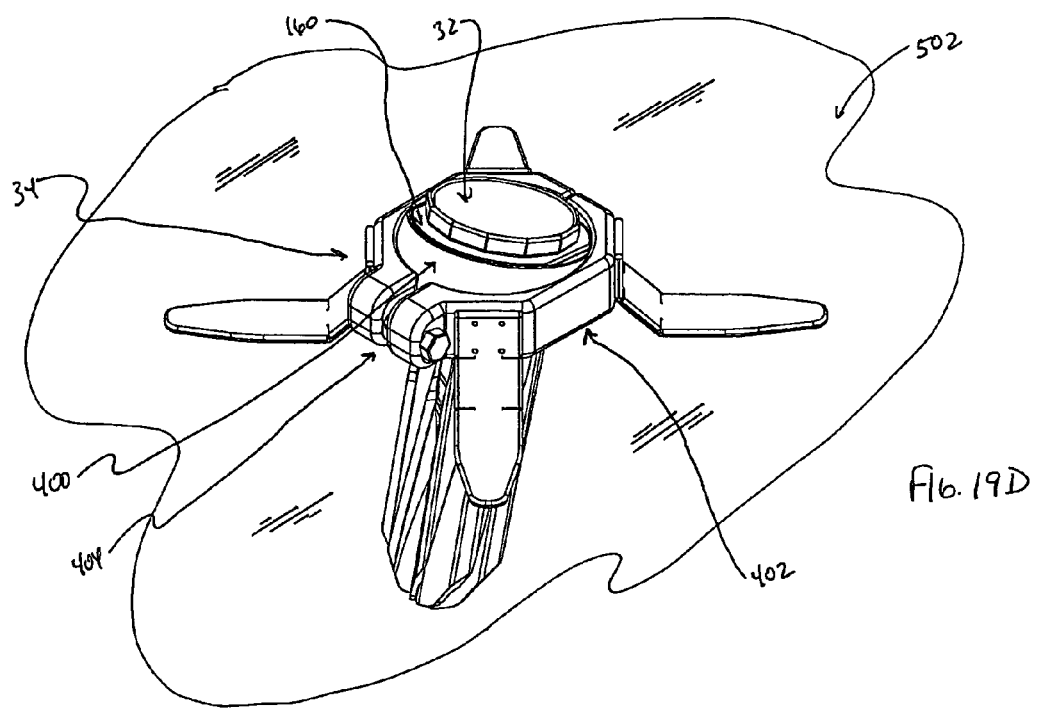
Figure 19E:
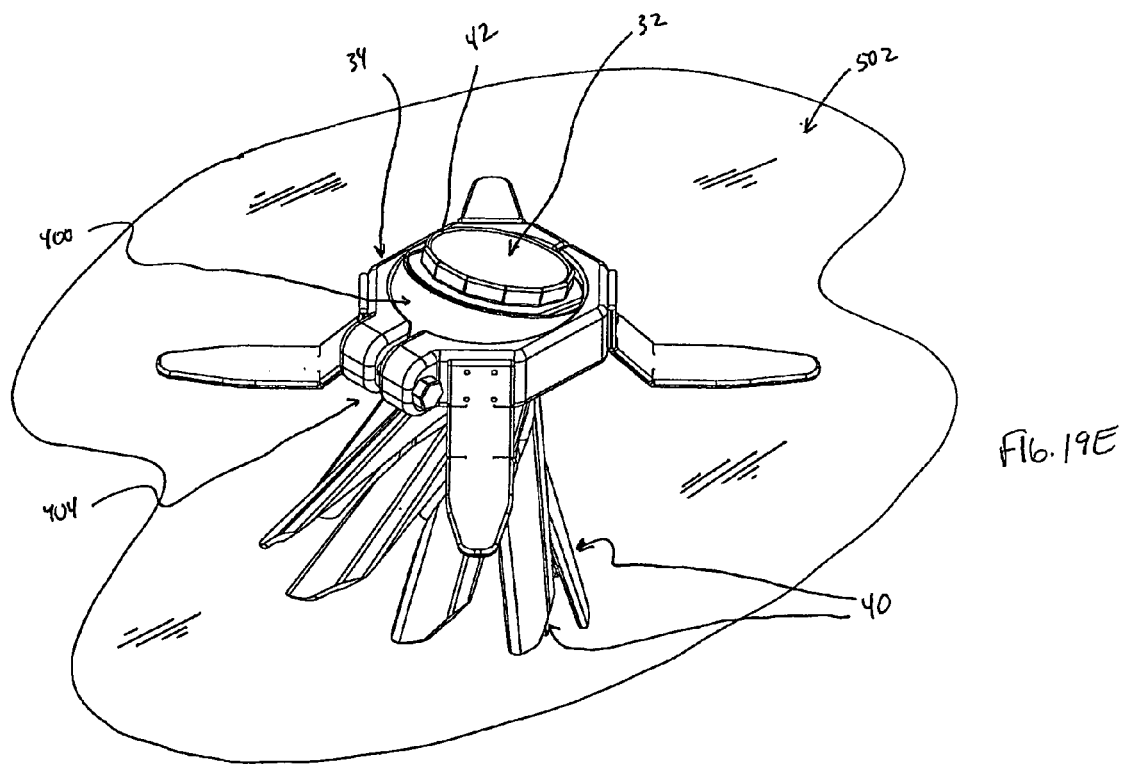

With other embodiments of surgical access systems of the present disclosure, the anchoring device 34 is provided. The anchoring device 34 is initially located over the incision 500 in the patient's skin 502 as shown in FIG. 19A. Where provided, the formatted bottom surface 466 (FIG. 17D) of the platforms 406 can be more robustly connected to the patient (e.g., via surgical drapes (not shown) surrounding the incision 500). For example, FIG. 19B schematically illustrates surgical drape(s) 504 conventionally arranged on the patient's skin 502 in close proximity to the incision 500. The platforms 406 can be pivoted from the arrangement shown, bringing the corresponding bottom surface 466 into secured engagement with the surgical drape 504 (e.g., via Velcro, adhesive, etc., carried by the bottom surface 466). Thus, a separate mounting frame assembly arranged about the patient is not required to stabilize the anchoring device 34 as is otherwise required with conventional surgical retractors. Regardless, with the port access device 32 arranged in the contracted state, and the blades 40 are inserted through the aperture 420 and into the surgical field as represented by FIGS. 19C and 19D. As a point of reference, the skin 502 is represented in FIGS. 19C-19E as being transparent so as to illustrate the blades 40 beneath the skin 502. The port access device flange 160 is mounted to the receiving body 400 as described above, thereby spatially holding the port access device 32 relative to the anchoring device 34. With the locking mechanism 404 in an unlocked arrangement, the receiving body 400, and thus the port access device 32, is rotated relative to the outer frame 402 (and thus relative to the patient). Once a desired orientation of the port access device 32 has been obtained, the locking mechanism 404 is operated to lock the receiving body 400 (and thus the port access device 32) relative to the outer frame 402 (and thus relative to the patient). The port access device 32 can then be operated as described above to maneuver the blades 40 into the expanded state, enlarging the surgical field and retracting contacted tissue, organs, etc., as generally reflected by FIG. 19E. Surgical instruments (not shown) are deployed through the port member 42 as described above. Where desired, a spatial orientation of the port access device 32 relative to the patient can be altered at any point during the procedure by simply operating the locking mechanism 404 to release, then re-secure, the receiving body 400 (and thus the port access device 32).

The surgical access systems of the present disclosure are highly suitable for performing a wide variety of surgical procedures. In some embodiments, the surgical access systems of the present disclosure are beneficially utilized with bariatric or other abdominal cavity procedures (e.g., gastric band placement, cholecystectomy, appendectomy, splenectomy, sleeve gastrectomy, vascular graft placement, nephrectomy, cystectomy, hysterectomy, gastric electrode placement, etc.). Other procedures apart from the abdominal cavity can also greatly benefit from the surgical access systems of the present disclosure. By scaling the various components (e.g., the blades), the surgical access systems of the present disclosure can be employed for a wide range of procedures, such as, but not limited to, breast exploration/mass excision, gynecological/anal explorations and operations, etc.

The surgical access systems of the present disclosure provide a marked improvement over previous designs. The systems provide, in one unit, the desired surgical aspects of access, retraction and visualization. Unlike laparoscopic techniques, use of the surgical access systems of the present disclosure eliminates the need for carbon dioxide insufflation (with abdominal cavity procedures) and provides direct visualization of the surgical field. Moreover, the cost-prohibitive nature of laparoscopic equipment is not at issue. Conversely, as compared to conventional open surgical procedures, the surgical access systems of the present disclosure require a relative short incision, thereby reducing patient trauma and recovery. Further, surgery can be conducted under IV sedation/local anesthesia without general anesthesia and intubation. Also, since surgical field retraction is achieved by the system itself, the surgical assistant normally assisting with operation of the separated retractor tool is free to support the surgeon as needed, or need not be present.

Although the present disclosure has been described with reference to preferred embodiments, workers skilled in the art will recognize that changes can be made in form and detail without departing from the spirit and scope of the present disclosure.

What is claimed is:

1. A surgical access system comprising:
a port access device including:
a port member defining a central passageway extending along a central longitudinal axis;
a plurality of blades circumferentially arranged about the longitudinal axis to collectively define an access region open to and extending distally from the central passageway, wherein each of the blades terminates at a tip opposite the port member; and
an articulation mechanism including a drive collar and configured to define a first pivot point along a length of each of the blades, each of the first pivot points establishing an axis of rotation that extends through the port member, the articulation mechanism being operable to articulate the blades between:
a collapsed state in which the tips collectively define a first diameter,
an expanded state in which the tips collectively define a second diameter greater than the first diameter,
wherein the articulation mechanism is configured such that the blades rotate about the corresponding first pivot point, and the first pivot points move longitudinally relative to the port member parallel with the longitudinal axis, in transitioning between the collapsed and expanded states.

2. The surgical access system of claim 1, wherein each of the blades pivots in a respective plane that is substantially tangent to a circumference of the port member in transitioning between the first and second states.

3. The surgical access system of claim 1, wherein the tips are co-planar in the first and second states.

4. The surgical access system of claim 1, wherein the plurality of blades are identical.

5. The surgical access system of claim 1, wherein the plurality of blades includes at least six blades.

6. The surgical access system of claim 1, wherein the articulation mechanism is configured to transition between the collapsed and expanded states with rotation of the port member.

7. The surgical access system of claim 1, wherein the articulation mechanism further establishes a second pivot point along a length of each of the blades, and further wherein the articulation mechanism is configured such that each of the blades rotate about the corresponding second pivot point in transitioning between the collapsed and expanded states.

8. The surgical access system of claim 7, wherein the articulation mechanism is configured such that the second pivot points move longitudinally relative to the port member in transitioning between the collapsed and expanded states.

9. The surgical access system of claim 8, wherein the articulation mechanism includes a plurality of links, respective ones of which are connected to respective ones of the blades at the corresponding second pivot point.

10. The surgical access system of claim 9, wherein the articulation mechanism further includes a hub rotatably mounted to the port member and pivotably connected to each of the links.

11. The surgical access system of claim 10, wherein the drive collar is threadably mounted to the port member and pivotably connected to each of the blades at the corresponding first pivot point.

12. The surgical access system of claim 11, wherein the articulation mechanism is configured such that rotation of the port member relative to the hub imparts a longitudinal movement on to the drive collar.

13. The surgical access system of claim 12, wherein the articulation mechanism is configured such that longitudinal movement of the drive collar applies a force on to the each of the blades at the corresponding first pivot point, with the blades rotating about the corresponding second pivot point in response to the force.

14. The surgical access system of claim 13, wherein the hub remains stationary as the blades transition between the collapsed and expanded states.

15. The surgical access system of claim 1, wherein the port access device further includes:
   a first LED mounted to an interior surface of a first one of the blades; and
   a second LED mounted to an interior surface of a second one of the blades.

16. The surgical access system of claim 1, further comprising:
   an illumination assembly including a light ring device configured to be selectively connected to the port access device and including a light source arranged to emit light toward the access region upon connection of the light ring device with the port access device.

17. The surgical access system of claim 16, wherein the illumination assembly further includes a transparent tube couple to the port member for transmitting light from the light ring device.

18. The surgical access system of claim 1, wherein at least one of the blades includes:
   a blade body forming the tip and a mounting end opposite the tip; and
   a shaft removably attached to the mounting end, the first pivot point being formed along the shaft.

19. The surgical access system of claim 1, further comprising:
   an anchoring device configured to selectively receive and maintain the access port device relative to a patient.

20. The surgical access system of claim 19, wherein the access port device further includes a flange associated with, and projecting radially outward relative to, the port member, and further wherein the anchoring device includes:
   a receiving apparatus forming an aperture sized to permit passage of the blades in the collapsed state and to receive the flange; and
   a plurality of platforms extending from the receiving apparatus and configured for securement to a patient.

21. The surgical access system of claim 20, wherein the receiving apparatus includes:
   an outer frame member defining an interior socket surface; and
   a receiving body defining a semi-spherical outer surface;
   wherein the receiving body is rotatably disposed within the frame member such that the interior socket surface and the semi-spherical outer surface combine to define a ball joint;
   and further wherein the receiving member defines the aperture for selectively engaging the flange.

22. The surgical access system of claim 21, wherein the receiving apparatus further includes a locking mechanism including a fastener and configured to selectively inhibit movement of the receiving body relative to the outer frame.

* * * * *

UNITED STATES PATENT AND TRADEMARK OFFICE
CERTIFICATE OF CORRECTION

PATENT NO. : 9,072,501 B2  
APPLICATION NO. : 13/833156  
DATED : July 7, 2015  
INVENTOR(S) : Hector J. Menchaca et al.

It is certified that error appears in the above-identified patent and that said Letters Patent is hereby corrected as shown below:

In the Specification

Column 2, line 39, delete "stated" and insert in place thereof --state--.

Column 2, line 62, delete "stated" and insert in place thereof --state--.

Column 3, line 28, delete "FIG. 1" and insert in place thereof --FIG. 1A--.

Column 3, line 66, delete "view" and insert in place thereof --views--.

Column 9, line 30, delete "stated" and insert in place thereof --state--.

Column 10, line 44, delete "points Pb" and insert in place thereof --points P1--.

Column 14, line 21, delete "and in" and insert in place thereof --and is--.

Column 14, line 43, delete "aperture sized 420" and insert in place thereof --aperture 420 sized--.

Column 14, line 47, delete "stated" and insert in place thereof --state--.

Column 15, line 21-22, delete "maintain" and insert in place thereof --maintaining--.

Column 15, line 56, delete "has having" and insert in place thereof --as having--.

Signed and Sealed this  
Twenty-sixth Day of April, 2016

Michelle K. Lee  
*Director of the United States Patent and Trademark Office*